US008580830B2

(12) United States Patent
Leichs et al.

(10) Patent No.: US 8,580,830 B2
(45) Date of Patent: Nov. 12, 2013

(54) NON-MUCOADHESIVE FILM DOSAGE FORMS

(75) Inventors: Christian Leichs, Alfdorf (DE); Armin Breitenbach, Leverkusen (DE); Ingo Lehrke, Cologne (DE); Paolo Galfetti, Comasco (IT)

(73) Assignees: Labtec GmbH (DE); APR Applied Pharma Research S.A. (CH)

( * ) Notice: Subject to any disclaimer, the term of this patent is extended or adjusted under 35 U.S.C. 154(b) by 782 days.

(21) Appl. No.: 12/443,414

(22) PCT Filed: Oct. 2, 2007

(86) PCT No.: PCT/EP2007/008579
§ 371 (c)(1),
(2), (4) Date: Mar. 26, 2010

(87) PCT Pub. No.: WO2008/040534
PCT Pub. Date: Apr. 10, 2008

(65) Prior Publication Data
US 2010/0173940 A1 Jul. 8, 2010

Related U.S. Application Data

(60) Provisional application No. 60/848,965, filed on Oct. 2, 2006.

(51) Int. Cl.
*A61K 31/425* (2006.01)
*A61K 9/00* (2006.01)

(52) U.S. Cl.
USPC ........... 514/365; 424/400; 424/484; 424/487; 424/488

(58) Field of Classification Search
None
See application file for complete search history.

(56) References Cited

U.S. PATENT DOCUMENTS

| | | | |
|---|---|---|---|
| 4,136,162 | A | 1/1979 | Fuchs et al. |
| 5,700,478 | A | 12/1997 | Biegajski et al. |
| 5,800,832 | A | 9/1998 | Tapolsky et al. |
| 5,985,684 | A | 11/1999 | Marshall et al. |
| 6,520,329 | B1 | 2/2003 | Fuchs et al. |
| 6,750,921 | B1 | 6/2004 | George |
| 7,067,116 | B1 | 6/2006 | Bess et al. |
| 2005/0147653 | A1* | 7/2005 | Yasuda et al. ............... 424/443 |

FOREIGN PATENT DOCUMENTS

| | | |
|---|---|---|
| CN | 1565429 | 1/2005 |
| CN | 1652824 | 8/2005 |
| EP | 0460588 | 12/1991 |
| EP | 1353857 | 1/2002 |
| WO | WO 01/62621 | 8/2001 |
| WO | WO 02/059012 | 8/2002 |
| WO | WO 03/093260 | 11/2003 |
| WO | WO 2005/080381 | 9/2005 |
| WO | WO 2006/056161 | 6/2006 |
| WO | WO 2006/074951 | 7/2006 |
| WO | WO 2007/125533 | 11/2007 |

OTHER PUBLICATIONS

Liang, A.C., et al. Fast-dissolving intraoral drug delivery systems. Expert Opinion on Therapeutic Patents, vol. 11, No. 6, pp. 981-986, Jan. 1, 2001.
International Search Report for PCT/EP2007/008579 mailed Nov. 18, 2008.
International Preliminary Report on Patentability and Written Opinion for PCT/EP2007/008579 dated Apr. 7, 2009.
Food & Drug Administration, Center for Drug Evaluation & Research, Guidance for Industry: Statistical Procedures for Bioequivalence Studies Using a Standard Two-Treatment Crossover Design, Jul. 1992.
Walton, Harold F., Principles of Ion Exchange. *Chromatography*. pp. 312-343.

* cited by examiner

*Primary Examiner* — Sreeni Padmanabhan
*Assistant Examiner* — Jody Karol
(74) *Attorney, Agent, or Firm* — Clark G. Sullivan; Troutman Sanders LLP

(57) ABSTRACT

Orally disintegrating film dosage forms for delivering active pharmaceutical agents, methods of formulating the dosage forms to retard absorption through the oral mucosa, and methods of using the dosage forms for the treatment of various medical conditions are provided.

12 Claims, 5 Drawing Sheets

X-ray diffraction pattern for donepezil HCl Form I.

X-ray diffraction pattern for ondansetron base Form B

NON-MUCOADHESIVE FILM DOSAGE FORMS

RELATIONSHIP TO PRIOR APPLICATIONS

This application claims priority to U.S. Provisional Application No. 60/848,965, filed Oct. 2, 2006 (now abandoned).

FIELD OF THE INVENTION

The present invention relates to orally disintegrating film dosage forms for delivering active pharmaceutical agents, methods of formulating the dosage forms to promote gastrointestinal absorption comparable to immediate release solid oral dosage forms, and to methods of using the dosage forms for the treatment of various medical conditions.

BACKGROUND OF THE INVENTION

Orally administered film strip dosage forms have been recently developed for the pharmaceutical industry, and are currently used for the sale of several popular over-the-counter drug products, including Listerine® breath strips, Triaminic® thin strips (active agent=diphenhydramine HCl), and Sudafed PE™ quick dissolve strips (active ingredient=phenylephrine HCl). The absolute bioavailability of diphenhydramine when ingested orally is approximately 61%, and the time to maximum serum concentration is about 3-4 hours. Phenylephrine is subject to extensive presystemic metabolism in the gut wall, such that the absolute bioavailability of phenylephrine when ingested orally is approximately 40% relative to intravenous dosing, and peak plasma concentrations are achieved in about 1-2 hours.

In addition, several manufacturers have proposed formulations that could be used to deliver prescription drugs. The vast majority of these formulations are "mucoadhesive" formulations designed for adhesion of the dosage form to mucosal tissue in the mouth, and transmission of the drug from the dosage form through the mucosal tissue into the systemic circulation. As described in U.S. Pat. No. 6,750,921 to Kim et al., film-forming agents have been used to manufacture drug delivery formulations for percutaneous or transdermal application, but these necessarily involve an adhesive composition to retain the agent in situ long enough to cause sustained release of the active ingredient. Bioerodible films are described in Tapolsky et al., U.S. Pat. No. 5,800,832. The films have an adhesive layer and a non-adhesive backing layer and are intended to adhere to the mucosal surface. Biegajski et al., U.S. Pat. No. 5,700,478, describes a water-soluble pressure-sensitive mucoadhesive suitable for use in a mucosal-lined body cavity.

The purported advantage of these mucoadhesive films resides in their ability to bypass the gastrointestinal tract, and barriers in the gastrointestinal tract to drug absorption such as first pass metabolism and decomposition of the active ingredient in the stomach. An additional advantage for these dosage forms, when compared to tablets, capsules and other dosage forms that must be swallowed, is that some patient populations have difficulty swallowing, such as children and the elderly.

Until now the prior art has been focused principally on improving the delivery profile of a given pharmaceutical agent with this dosage form, by increasing its rate of dissolution or absorption, or bypassing metabolic processes that reduce the bioavailability of the drug. The prior art has not appreciated that an innovator's drug product, be it a tablet, capsule, or other oral dosage form, has already proven itself effective through rigorous clinical testing, and that the innovator's product may already provide the optimum bioavailability of pharmaceutical agent. What is needed is a film product that mimics the pharmacokinetics of an innovator's product, and that follows the same metabolic and bioabsorption pathways as the innovator's product, to ensure that the dosage form achieves the proven clinical efficacy of the innovator product.

OBJECTS OF THE INVENTION

Accordingly, it is an object of the present invention to provide non-mucoadhesive orally disintegrating film dosage forms that mimic the pharmacokinetic profile of orally administered drug products such as tablets, capsules, liquid suspensions, and orally dissolving/dispersing tablet (ODT).

Another object of the invention is to provide non-mucoadhesive orally disintegrating film dosage forms that follow the same metabolic and bioabsorption pathways through the gastrointestinal tract as existing orally administered drugs, such as tablets, capsules, liquid suspensions, and orally dissolving/dispersing tablet (ODT).

Still another object of the present invention is to provide methods of formulating and testing non-mucoadhesive orally disintegrating film dosage forms so that they follow the same metabolic and bioabsorption pathways, and obtain the same pharmacokinetic profiles, as existing orally administered drugs such as tablets, capsules, liquid suspensions, and orally dissolving/dispersing tablet (ODT).

Another object of the present invention is to provide methods of treatment using the film dosage forms of the present invention, and methods that promote bioequivalence to orally administered drug products such as tablets, capsules, liquid suspensions, and orally dissolving/dispersing tablet (ODT).

Yet another object of the present invention is to provide techniques and methodologies for retarding the absorption of drugs from orally disintegrating films through the oral mucosa.

SUMMARY OF THE INVENTION

The present invention provides film dosage forms that are formulated or administered for gastrointestinal absorption of the active pharmaceutical agent, and that are bioequivalent to and interchangeable with existing orally administered drug products. These film dosage forms are non-mucoadhesive; they quickly disintegrate in the mouth when exposed to saliva; and they are absorbed predominantly through the gastrointestinal tract. Most importantly, these dosage forms are specially formulated to meet exacting bioavailability requirements, or to be bioequivalent to existing orally administered dosage forms.

Therefore, in a first principal embodiment, the invention provides a non-mucoadhesive orally disintegrating film, able to disintegrate upon contact with saliva in the buccal cavity within about sixty seconds, comprising a defined amount of an active pharmaceutical agent, a hydrophilic binder and a water-soluble diluent, wherein: (a) said film is formulated for delivery of said active agent through the gastrointestinal tract when applied to the tongue; (b) said film comprises from about 0.05% to about 50% (w/w) of said active pharmaceutical agent, based on the total weight of the formulation; and (c) said film is bioequivalent to an immediate release tablet or orally dissolving/dispersing tablet (ODT) that comprises said active pharmaceutical agent in said defined amount.

In one embodiment, the immediate release tablet or orally dissolving/dispersing tablet (ODT) is characterized by slow or delayed bioavailability (i.e. a "slowly bioavailable drug"). The inventors have developed orally disintegrating film dosage forms which, it is believed, will unexpectedly be bioequivalent to these conventional "slowly bioavailable drugs," without any substantial modification of the release characteristics from the film dosage form, as long as the film can disintegrate when placed on the tongue within about sixty seconds. Thus, for example, the immediate release dosage form can be characterized by:

- a $T_{max}$ (i.e. time to maximum plasma concentration) of greater than about 1.5 hours, 2.0 hours, 2.5 hours, 3.0 hours, 3.5 hours, 4.0 hours, 4.5 hours or even 5.0 hours;
- a disintegration time of greater than about 10 or 20 minutes, but less than about 90 or 60 minutes;
- a 90% dissolution time of greater than about 10 or 20 minutes, but less than about 90 or 60 minutes; and/or
- a film coating that delays the release and absorption of active ingredient from the dosage form.

Of course, the invention could also be practiced with drugs having other pharmacokinetic profiles, and in other embodiments the $T_{max}$ of the drug is less than 3.0, 2.5, 2.0, 1.5 or 1.0 hours.

In another embodiment, the film strip of the present invention, or the immediate release dosage form, can be defined by its pharmacokinetics, and in one embodiment, the film strip or immediate release dosage form has an absolute bioavailability of greater than 65%, 75%, 85% or even 95% when administered orally. In another embodiment, the film strip or immediate release dosage form has an absolute bioavailability that is greater than about 45%, 50%, or 55%, and peak plasma concentrations ($C_{max}$) in less than 3.0, 2.5 or 2.0 hours. Finally, because the film dosage form is specially formulated or administered for gastrointestinal absorption, the film dosage form has a comparable absolute bioavailability or $T_{max}$ as an immediate release tablet or capsule or orally dissolving/dispersing tablet (ODT) that comprises the same amount of active pharmaceutical agent.

The films themselves, and the methods of using the films, are characterized by a number of features that ensure their bioequivalence to a comparable immediate release tablet or capsule or orally dissolving/dispersing tablet (ODT), including:

- the films may be engineered or used so that the active pharmaceutical agent is swallowed and absorbed predominantly or entirely through the gastrointestinal tract, instead of being absorbed through the oral mucosa;
- if necessary, the films or active pharmaceutical agents may be formulated so that absorption of active pharmaceutical agent through the oral mucosa is retarded;
- the films are typically designed for rapid disintegration when taken orally, and are most often swallowed in less than thirty or sixty seconds after administration;
- the films are usually applied directly onto the tongue to promote mixing with the saliva and subsequent swallowing of the active ingredient, and thereby discourage mucosal absorption; and
- water could be additionally swallowed within about thirty or sixty seconds after administration of the film, to further promote swallowing of the active agent and gastrointestinal absorption.

A particularly preferred drug of the present invention is a donepezil film strip, which demonstrates bioequivalence to existing immediate release tablets of donepezil hydrochloride, and which exhibits a peak plasma concentration of donepezil in from about three to about four hours. Another preferred drug is an ondansetron film strip, which is characterized by an absolute bioavailability of ondansetron of from about 45% to about 75%, and which is formulated as a base to retard absorption through the oral mucosa. Other preferred drugs are set forth in the detailed description of invention and examples which follow.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE INVENTION

Figure 1:
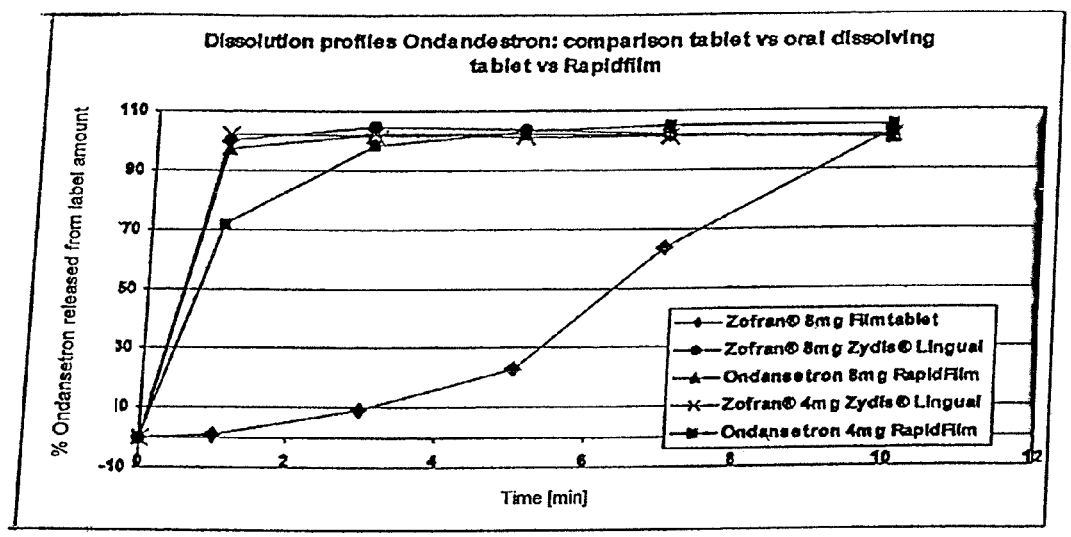
FIG. 1 is a comparison of dissolution profiles over time comparing three commercially available formulations of ondansetron with two ondansetron RapidFilm formulations, as described in Table 4. The upper line at 1 minute is Zofran® 4 mg Zydis® Lingual; the second line at 1 minute is Zofran® 8 mg Zydis® Lingual; the third line is ondansetron 8 mg RapidFilm; the fourth line is ondansetron 4 mg RapidFilm; the bottom line is Zofran® 8 mg Filmtablet.

The present invention may be understood more readily by reference to the following detailed description of preferred embodiments of the invention and the Examples included therein.

DEFINITIONS AND USE OF TERMS

As used in this specification and in the claims which follow, the singular forms "a," "an" and "the" include plural referents unless the context clearly dictates otherwise. Thus, for example, reference to "an ingredient" includes mixtures of ingredients, reference to "an active pharmaceutical agent" includes more than one active pharmaceutical agent, and the like.

The term "disintegrate" has its usual and customary meaning in the pharmaceutical arts, as described in <701> of the U.S. Pharmacopoeia (2005 USP/NF) for uncoated tablets, using a basket rack assembly operating at 30 cycles per minute through a distance of 5.5 cm, in a disintegration medium at 37° C. When disintegration requirements are discussed herein, they are preferably met under the foregoing testing conditions, at a pH of 4.0 or 6.8. A film or other dosage form is said to be "disintegrated" if it is completely disintegrated, a state in which any residue of the unit remaining on the screen of the test apparatus, or in the mouth, is a soft mass having no palpably film core, or fragments of a tablet coating or capsule shell. Disintegration thus does not imply complete dissolution of the dosage unit or even the active constituent, although a dissolved dosage unit would typically be completely disintegrated. When reference to Ph. Eur. 2.9.1 (disintegration) is made herein, it will be understood that the disintegration conditions described above under <701> USP can also be employed.

The term "dissolution" also has its usual and customary meaning in the pharmaceutical arts, as described in <711> and <724> of the U.S. Pharmacopoeia (2005 USP/NF). Therefore, a film is said to be "dissolved" if, upon testing by the method of U.S. Pharmacopoeia (2005 USP/NF), the amount of active agent dissolved in the dissolution medium exceeds a predetermined percentage. When dissolution conditions are given, it will be understood that stirring preferably occurs in 0.1N hydrochloric acid buffer (pH=2), or at pH 1.2, pH 4.0 or 6.8, at 37° C., using the paddle method at 50 rpm in a type II dissolution apparatus.

The term "immediate release," when used in this document, refers to a dosage form that allows the drug to dissolve in the gastrointestinal contents, with no intention of delaying or prolonging the dissolution or absorption of the drug. The term includes tablets, capsules, liquid suspensions, orally disintegrating/dispersing tablet (ODT), and other dosage forms intended for immediate release of active ingredient upon administration (preferably oral administration). In contrast, a "modified release" dosage form is a dosage form whose drug release characteristics of time course and/or location are chosen to accomplish therapeutic or convenience objectives not offered by conventional dosage forms such as a solution or immediate release dosage form. Modified release solid oral dosage forms include both delayed and extended release drug products.

An "immediate release" dosage form as used herein preferably refers to a dosage form adapted to release at least 80% or 90% of an active pharmaceutical ingredient in 60 minutes or less when measured in a type II dissolution apparatus (as described in <711> and <724> of the U.S. Pharmacopoeia (2005 USP/NF)), in 0.1N hydrochloric acid buffer (pH=2), or at pH 1.2, pH 4.0 or 6.8, at 37° C. In a preferred embodiment, at least 80%, 90% or 100% is dissolved in no more than 45 or 30 minutes. Stirring preferably occurs using the paddle method at 50 rpm. Finally, it will be understood that when reference to Ph. Eur. 2.9.3 (paddle over disc) is made herein, the foregoing dissolution conditions under <711> and <724> of the U.S. Pharmacopoeia (2005 USP/NF) can be applied.

An immediate release solid oral dosage form is considered "rapidly dissolving" when not less than 80% of the label amount of the drug substance dissolves (i.e. releases) within 15 minutes in each of the following media: (1) pH 1.2, (2) pH 4.0, and (3) pH 6.8, in accordance with Q6 ICH-guideline.

A "orally dissolving or orally dispersible tablet" ("ODT") refers to an uncoated tablet intended to be placed in the mouth where it can disperse rapidly before being swallowed, as described in Eur. Ph. 5.0. An ODT disintegrates within three minutes when tested according to the disintegration testing described herein.

The term "non-mucoadhesive" means that the dosage form is not designed for administration of the active pharmaceutical agent through the oral mucosa. I.e. the dosage form is not designed to adhere to the mucosal surfaces of the buccal cavity as an intact film or disintegrated film residue.

Unless specified otherwise, the term "wt. %" as used herein with reference to the final product (i.e., the film, as opposed to the formulation used to create it), denotes the percentage of the total dry weight contributed by the subject ingredient. This theoretical value can differ from the experimental value, because in practice, the film typically retains some of the water and/or ethanol used in preparation.

When doses are given for a drug and its salt, it will be understood that the calculated dose is based on the molecular weight of the active pharmaceutical ingredient, which includes the cationic and anionic species in the case of a salt, and just the base when the active principle is not present as a salt. In addition, when reference is made to the salt of a drug and pharmaceutically acceptable salts thereof, it will be understood that salts of the base form of the base drug are intended.

When ranges are given by specifying the lower end of a range separately from the upper end of the range, it will be understood that the range can be defined by selectively combining any one of the lower end variables with any one of the upper end variables that is mathematically possible.

When used herein the term "about" or "ca." will compensate for variability allowed for in the pharmaceutical industry and inherent in pharmaceutical products, such as differences in product strength due to manufacturing variation and time-induced product degradation. The term allows for any variation which in the practice of pharmaceuticals would allow the product being evaluated to be considered bioequivalent to the recited strength of a claimed product.

The term "absolute bioavailability" refers to the availability of the active drug in systemic circulation after non-intravenous administration (i.e., after oral, rectal, transdermal, subcutaneous administration). In order to determine absolute bioavailability of a drug, a pharmacokinetic study must be done to obtain a plasma drug concentration versus time plot for the drug after both intravenous (IV) and non-intravenous administration. The absolute bioavailability is the dose-corrected area under curve (AUC) non-intravenous divided by AUC intravenous.

When pharmacokinetic parameters are given herein (i.e. $T_{max}$, absolute bioavailability, etc.), it will be understood that they can refer to the mean, median, or individual observed pharmacokinetics, and that mean pharmacokinetics are intended when claimed unless stated to the contrary.

Discussion

As discussed above, the invention provides a physiologically acceptable film that is particularly well adapted to disintegrate rapidly when placed on the tongue of a patient, and to facilitate gastrointestinal absorption of the pharmaceutically active agent. The film and active agent need not dissolve entirely in the mouth, and preferably the film is not entirely dissolved. When tested according to Ph. Eur. 2.9.3, paddle over disc, the film preferably dissolves (at least 80% or 100% active agent release) within about 15, 10 or 5 minutes, when tested at pH 1.2, 4.0 or 6.8.

The film may also be characterized by the time it takes to disintegrate completely, and it preferably disintegrates to a soft residue within about 10, 20, 30 or 60 seconds of administration, after which it is swallowed. These disintegration times are preferably observed in the oral cavity when the film is administered, as well as when tested for disintegration using the method described in Ph. Eur. 2.9.1. The prompt disintegration and swallowing of the film helps to assure gastrointestinal absorption of the dosage form. The film is not of the conventional mucoadhesive type, designed to deliver active agent transmucosally.

In one embodiment, the film is defined by its long $T_{max}$, and in various embodiments, the film has a $T_{max}$ of greater than about 3.0, 3.5, 4.0, 4.5, or 5.0 hours. Alternatively or in addition, the film can be defined by the absolute bioavailability (i.e. total extent of absorption) of the active ingredient and, in various embodiments, the film has an absolute bioavailability that is greater than about 45%, 55%, 65%, 75%, 85% or even 95%. In still another embodiment, the film is defined by the rate or extent of absorption of active agent into the bloodstream, in addition or alternatively to the absolute bioavailability of the active agent. For example, the film can be defined by $T_{max}$ (i.e. time to maximum concentration of the active agent in plasma) and, in various embodiments, the film has a $T_{max}$ less than about 3.0, 2.5, 2.0 or even 1.5 or 1.0 hours. Alternatively or in addition, the film can be defined by an absolute bioavailability greater than about 45%, 50%, or 55%.

Therefore, in another embodiment the invention provides a non-mucoadhesive orally disintegrating film, able to disintegrate upon contact with saliva in the buccal cavity within about sixty seconds, comprising a defined amount of an active pharmaceutical agent, or a pharmaceutically acceptable salt thereof, a hydrophilic binder and a water-soluble diluent, wherein: (a) said film is formulated for delivery of said active agent through the gastrointestinal tract when applied to the tongue; (b) said film comprises from about 0.05% to about 50% (w/w) of said active pharmaceutical agent, based on the total weight of the formulation; and (c) said film is characterized by one or more of the following pharmacokinetic parameters: (i) a $T_{max}$ of greater than about 4.5 hours; (ii) an absolute bioavailability of greater than 65%, and optionally a $T_{max}$ greater than about 1.5 hours; or (iii) a $T_{max}$ of less than about 3.0 hours, and an absolute bioavailability greater than about 45%.

In another embodiment, the invention is defined by its bioequivalence to an immediate release dosage tablet or capsule or orally dissolving/dispersing tablet (ODT) that contains the same amount of active pharmaceutical agent. In particular, the invention provides a non-mucoadhesive orally disintegrating film, able to disintegrate upon contact with saliva in the buccal cavity within about sixty seconds, comprising a defined amount of an active pharmaceutical agent, or a pharmaceutically acceptable salt thereof, a hydrophilic binder and a water-soluble diluent, wherein: (a) said film is formulated for delivery of said active agent through the gastrointestinal tract when applied to the tongue; (b) said film comprises from about 0.05% to about 50% (w/w) of said active pharmaceutical agent, based on the total weight of the formulation; and (c) said film is bioequivalent to an immediate release tablet or capsule or orally dissolving/dispersing tablet (ODT) that comprises said active pharmaceutical agent or a pharmaceutically acceptable salt thereof in said defined amount (i.e. a "reference product").

The reference product can be defined by various pharmacokinetic or physical properties. For example, the reference product could be characterized by its absolute bioavailability, and preferably the absolute bioavailability is greater than about 65%, 75%, 85% or even 95% when administered orally, and/or a $T_{max}$ greater than about or 4.5 hours. The reference product could also be characterized by its $T_{max}$ and/or absolute bioavailability, i.e. a $T_{max}$ less than about 3.0, 2.5, 2.0 or even 1.5 or 1.0 hours, and/or an absolute bioavailability greater than about 45%, 50%, or 55%.

Alternatively, the reference product could be characterized by its disintegration time which, in various embodiments could exceed 5, 10, 20, 30, 40 or 45 minutes, when tested according to Ph. Eur. 2.9.1, and preferably would be less than 60, 75 or 90 minutes. The reference product could also be defined by its dissolution time. Dissolution times for the comparative reference products of the present invention, when tested according to Ph. Eur. 2.9.3, based on the time it takes to dissolve 75, 80, 85, 90 or 95 wt. % of the drug substance, when tested at pH 1.2, 4.0 and/or 6.8, are preferably greater than about 5, 10, 20, 30, 40 or 45 minutes, and less than about 90, 75 or 60 minutes. In a preferred embodiment, the dissolution profile for the reference product is in accordance with the following specification: not less than 70, 80, 90 or 95% dissolved after 60 minutes when tested according to Ph. Eur. 2.9.3 (paddle over disc). In one embodiment, the reference product is a capsule, optionally characterized by a gelatin shell. In another embodiment, the reference product is a tablet, optionally characterized by a film or enteric coating. In another embodiment, the reference product is a orally dissolving/dispersing tablet (ODT).

The film can also be characterized by various physical characteristics, including its structure, size and shape. For example, in one embodiment, the film is a single layer homogeneous film. In another embodiment, the film has a weight of from about 30 to about 150 milligrams, preferably from about 40 to about 120 milligrams. The film may vary in thickness anywhere from about 10 to about 200 microns, and preferably does not exceed 8 or 7 $cm^2$ in surface area.

The invention also provides various methods of treatment, based on the particular active agent involved, that rely on one or more of several defining characteristics, including the placement of the dosage form on the tongue, swallowing the dosage form within ten, twenty, thirty, forty-five or sixty seconds, and swallowing the dosage form with or without water. In yet another embodiment, therefore, the invention provides a method of treatment comprising: (a) providing a non-mucoadhesive orally disintegrating film, able to disintegrate upon contact with saliva in the buccal cavity within about sixty seconds, comprising a defined amount of an active pharmaceutical agent, or a pharmaceutically acceptable salt thereof, a hydrophilic binder and a water-soluble diluent: (b) placing said film on the tongue to produce a disintegrated film residue; and (c) swallowing said residue within about sixty seconds of step (b), so that the pharmaceutical agent is predominantly absorbed through the gastrointestinal tract; wherein: (i) said film is bioequivalent to an immediate release tablet or capsule or orally dissolving/dispersing tablet (ODT) that comprises said active pharmaceutical agent or a pharmaceutically acceptable salt thereof in said defined amount; (ii) said film has a $T_{max}$ greater than about 4.5 hours; (iii) said film has an absolute bioavailability of greater than about 65%, and optionally a $T_{max}$ greater than about 1.5 hours; or (iv) said film has an absolute bioavailability of greater than about 45%, and a $T_{max}$ of less than about 3.0 hours; (v) said film has a $T_{max}$ less than about 1.5 hours.

Formulating for Bioequivalence

In still another embodiment, the invention provides methods of formulating the film dosage form, to ensure bioequivalence between the film and an immediate release dosage form containing the same amount of the same active pharmaceutical agent. In like manner, the invention provides film dosage forms that are formulated according to these methods, and methods of treatment that rely upon such dosage forms.

Thus, in another embodiment, the invention provides a method of making a bioequivalent non-mucoadhesive orally disintegrating film, comprising: (a) providing an orally swallowed dosage form that comprises an active pharmaceutical agent in a defined amount, and that is characterized by (i) gastrointestinal absorption when swallowed, and (ii) a first pharmacokinetic profile; (b) formulating a first batch of non-mucoadhesive orally disintegrating film, able to disintegrate upon contact with saliva in the buccal cavity within about sixty seconds, that comprises said active agent in said defined amount, and that is characterized by (i) a defined formulation, (ii) gastrointestinal absorption when dissolved orally, and (iii) a second pharmacokinetic profile that is bioequivalent to said first pharmacokinetic profile; and (c) clinically testing said orally administered dosage form and said orally disintegrating film for bioequivalence.

In still another embodiment the method further includes (a) measuring a first dissolution or disintegration profile for said orally disintegrating film from said first batch; (b) preparing a second batch of non-mucoadhesive orally disintegrating film that is characterized by said defined formulation; (c) measuring a second dissolution or disintegration profile for said orally disintegrating film from said second batch; and (d) comparing said first and second dissolution or disintegration profiles for equivalence or sameness (i.e. within acceptable deviations for pharmaceutical products in the pharmaceutical industry).

Bioequivalence Testing

Bioequivalence testing typically requires an in vivo test in humans in which the concentration of the active ingredient or active moiety, and, when appropriate, its active metabolite(s), in whole blood, plasma, serum, or other appropriate biological fluid is measured as a function of time. Defined as relative bioavailability ("BA"), bioequivalence ("BE") involves a comparison between a test and reference drug product. Although BA and BE are closely related, BE comparisons normally rely on (1) a criterion, (2) a confidence interval for the criterion, and (3) a predetermined BE limit.

A standard in vivo BE study design is based on the administration of either single or multiple doses of the test and reference products to healthy subjects on separate occasions, with random assignment to the two possible sequences of drug product administration. Statistical analysis for pharmacokinetic measures, such as area under the curve (AUC) and peak concentration ($C_{max}$), is preferably based on the so-called "two one-sided tests procedure" to determine whether the average values for the pharmacokinetic measures determined after administration of the test and reference products are comparable. This approach is termed average bioequivalence and involves the calculation of a 90% confidence interval for the ratio of the averages (population geometric means) of the measures for the test and reference products. To establish BE, the calculated confidence interval should fall within a BE limit, i.e. 80-125% for the ratio of the product averages. Further detail regarding BE procedures can be found in FDA's July 1992 Guidance Document entitled "Statistical Procedures for Bioequivalence Studies Using a Standard Two-Treatment Crossover Design," the contents of which are incorporated herein by reference.

Film Formulation

Preferred films according to the invention comprise a pharmaceutically active agent, a film-forming agent, and at least one of the following additional ingredients: water, antimicrobial agents, water soluble diluents such as plasticizing agents, softeners, and fillers, flavoring agents, saliva stimulating agents, cooling agents, stabilizers, surfactants, stabilizing agents, emulsifying agents, thickening agents, binding agents, coloring agents, sweeteners, fragrances, triglycerides, preservatives, polyethylene oxides, propylene glycol, and the like.

In a preferred embodiment, the film comprises one or more ingredients that act both as water soluble binding agents and hydrophilic polymers, such as polyvinyl alcohol, polyethylene glycol ("PEG"), propylene glycol, polyethylene oxide, and starches, celluloses, gelatines and the like. Therefore, when it is stated herein that a formulation comprises a water soluble binding agent and a hydrophilic polymer, it will be understood that these two agents may be describing one solitary ingredient. The finished film product preferably comprises from about 40 to about 80 wt. % of these ingredients, and more preferably from about 50 to about 75 wt. %. The active agent preferably makes up from 5 to 20 wt. % of the finished film formulation, more preferably from about 8 to about 15 wt. %. The formulation is also preferably "surfactant free." Alternatively, the formulation may contain one or more surfactants.

A preferred taste masking agent, which facilitates the dissolution of the product, and it is believed helps to maintain the amorphous state of certain active ingredients such as donepezil, is an aminoalkyl methacrylate copolymer such as that marketed as Eudragit E PO. The aminoalkyl methacrylate copolymer preferably contains diethyaminoethyl residues, and preferably comprises from about 20 to about 26 wt. % of such groups in a dry substance basis. The average molecular weight of the copolymer preferably ranges from about 120,000 to about 180,000, or from about 140,000 to about 160,000, most preferably about 150,000. Preferred methacrylic monomers include butyl methacrylate and methyl methacrylate. This agent is preferably present in the final film in an amount of from about 5 to about 25 wt. %, preferably from about 10 to about 20 wt. %, and more preferably from about 12 to about 18 wt. %. The copolymer is preferably micronized to an average particle size less than 100, 100, or 10 microns.

Another taste masking agent is a cyclodextrin or derivative thereof. This component is preferably present in the final film in an amount of from about 10 to about 50 wt. % or, in alternative embodiments, from about 10 to about 40 wt. %, or from about 20 to about 35 wt. %.

A preferred stabilizer, especially for donepezil films, is citric acid, especially anhydrous citric acid, and in a preferred embodiment the final product comprises from about 0.5 to about 2.0 wt. % citric acid, or from about 0.75 to about 1.25 wt. % citric acid.

Means for Retarding Buccal Absorption (or for Promoting GI Absorption)

Yet another embodiment relates to the orally disintegrating films themselves, and the means incorporated in the films for assuring that the active agent is absorbed through the gastrointestinal tract instead of the oral mucosa. Therefore, in still another embodiment, the invention provides an orally disintegrating film comprising: (a) an active pharmaceutical agent that is absorbable through the oral mucosa when dissolved; and (b) means for retarding absorption of said active pharmaceutical ingredient through the oral mucosa.

The active ingredient from the dosage form is preferably absorbed predominantly through the gastrointestinal tract. I.e. of the active ingredient absorbed, the predominant amount (greater then 60, 70, 80, 90, 95 and up to 100 wt. %) is preferably absorbed through the GI tract. Therefore, the means should be able to deliver greater than 60, 70, 80, 90 or 95 and up to 100 wt. % of the active ingredient to the gastrointestinal tract, through the natural process of swallowing, with or without additional water. The formulations can rely on various means for retarding absorption of the active ingredient through the oral mucosa, or promoting absorption through the gastrointestinal tract. The means should be able to deliver greater than 60, 70, 80, 90 or 95 and up to 100% of the active ingredient to the gastrointestinal tract, through the natural process of swallowing, with or without additional water. For some drugs, the means may simply comprise the particular film-forming agents employed in the film, and the absence of material quantities of agents that partition the active agent away from the saliva or the disintegrated residue toward the mucosal surfaces. For other drugs, which are more permeable through the oral mucosa, or for which only a small amount of mucosal absorption can be tolerated (due to bioequivalence requirements for the drug), it may be necessary to integrate a more proactive means for retarding gastrointestinal absorption, such as ion exchange resins that bind the active agent and prevent its ionization and dissolution upon disintegration of the film; pH adjusting agents that adjust the pH of the environment surrounding the dosage form to a pH that renders the active agent less permeable; and the use of less permeable salts and bases of active agents.

Suitable ion exchange resins are described generally in H. F. Walton in "Principles of Ion Exchange" (pp. 312 343), and particularly in U.S. Pat. No. 7,067,116 to Bess et al. Preferred ion exchange resins are water-insoluble and consist of a pharmacologically inert organic or inorganic matrix containing covalently bound functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g., modified cellulose and dextrans). The inorganic matrix can also be, e.g., silica gel modified by the addition of ionic groups. The covalently bound ionic groups may be strongly acidic (e.g., sulfonic acid), weakly acidic (e.g., carboxylic acid), strongly basic (e.g., quaternary ammonium), weakly basic (e.g., primary amine), or a combination of acidic and basic groups. In general, those types of ion exchangers suitable for use in ion exchange chromatography and for such applications as deionization of water are suitable for use in these controlled release drug preparations.

Suitable pH adjusting agents function by ionizing the active agent to a less permeable state. For an acidic active agent, one would adjust the pH of the solution to above the pKa of the active agent to give a neutral species; for a basic active ingredient, one would adjust the pH of the solution to below the pKa of the conjugate acid. Suitable pH adjusting agents for raising the pH of a solution include, for example, sodium carbonate, sodium bicarbonate, potassium carbonate, potassium bicarbonate, sodium phosphate, potassium phosphate, calcium carbonate, magnesium carbonate, sodium hydroxide, magnesium hydroxide, potassium hydroxide, and aluminum hydroxide. Suitable pH adjusting agents for lowering the pH of a solution include, for example, weak acids such as those containing carboxylic acid.

Another method for retarding the buccal absorption of active agent is to incorporate cyclodextrin in the product, particularly alpha-, beta- and gamma-cyclodextrin, derivatives and/or mixtures thereof. This component is preferably present in the final film in an amount of from about 10 to about 50 wt. % or, in alternative embodiments, from about 10 to about 40 wt. %, or from about 20 to about 35 wt. %.

Another method for retarding the buccal absorption of active agent is to incorporate acrylate polymers, such as Eudragite E P O, Eudragite R S, Eudragite R L, Eudragite L etc. and combinations thereof in the product. These components are preferably present in the final film in an amount of from about 10 to about 50 wt. % or, in alternative embodiments, from about 10 to about 40 wt. %, or from about 20 to about 35 wt. %.

Preferred Active Agents

Numerous active agents can be used in the practice of the current invention, in various crystalline forms. In a preferred embodiment, the active ingredient is present in an amorphous state in the final product. Numerous factors can influence the formation and stabilization of the amorphous state in the final product, including the length of polymer used to form the film, the high processing temperature, and the use of solvents.

A particularly preferred pharmaceutically active agent for use in this invention is donepezil hydrochloride, chemically known as (±) 2,3-dihydro-5,6-dimethoxy-2-[[1-(phenylmethyl)-4-piperidinyl]methyl]-1H-inden-1-one hydrochloride, and represented by the following chemical structure:

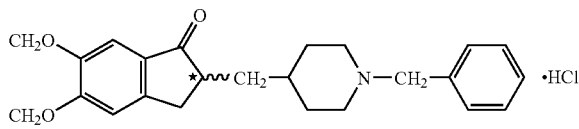

Therefore, in one embodiment based upon donepezil, the invention provides a donepezil film strip, i.e. a non-mucoadhesive orally disintegrating film, able to disintegrate upon contact with saliva in the buccal cavity within about sixty seconds, comprising (±) 2,3-dihydro-5,6-dimethoxy-2-[[1-(phenylmethyl)-4-piperidinyl]methyl]-1H-inden-1-one (donepezil), or a pharmaceutically acceptable salt thereof, in combination with a hydrophilic binder and a water-soluble diluent, wherein: (a) said film comprises from about 2.5 to about 20, preferably about 5 or 10, mg of donepezil or a pharmaceutically acceptable salt thereof; (b) donepezil hydrochloride is present in an amount from about 0.05% to about 50% (w/w), based on the total weight of the formulation; (c) said film has a $T_{max}$ of from about 3 to about 4 hours, and (d) said donepezil hydrochloride has an absolute bioavailability in said dosage form of about 100%. The donepezil is preferably present as donepezil hydrochloride, and the film is preferably characterized by the general formulations described herein.

Other embodiments relate to the use of donepezil film strips in the treatment of dementia, particularly dementia of the Alzheimer's type. Thus, in yet another embodiment, the invention provides a method of treating mild to moderate dementia in a human patient comprising administering to the tongue of said patient, preferably once daily, the donepezil films of the present invention. In a preferred embodiment, the treatment is accompanied by a step that promotes GI absorption of the donepezil, such as swallowing within about 60 seconds of administration, with or without water.

Various crystalline forms of donepezil hydrochloride are known in the art, including an amorphous state and five crystalline states designated Forms (I) to (V), as described more particularly in U.S. Pat. No. 5,985,684. In a particularly preferred embodiment, the donepezil hydrochloride is present in the final formulation substantially or completely in an amorphous state, more than 70, 80, 90, 95, 98 or 99% free of other crystalline forms of donepezil hydrochloride. The combination of amorphous donepezil and aminoalkyl methacrylate copolymer or a reduced quantity of beta-cyclodextrin has proven particularly useful, and results in a film product having excellent physical properties. The utility of the amorphous form might be attributable to its reluctance to transform into a solvated form, unlike Form I which, when treated with water, changes its solid state and converts into a solvate form.

In one embodiment the product is manufactured initially from Form I, and results in a final product that contains predominantly (if not completely) amorphous donepezil hydrochloride. It has been found that using Form I as the starting material results in a substantially better final product than starting with amorphous donepezil hydrochloride stabilized with known stabilizers, such as e.g. lactose. Therefore in still another embodiment, the invention provides a non-mucoadhesive orally disintegrating film, able to disintegrate upon contact with saliva in the buccal cavity within about sixty seconds, comprising donepezil hydrochloride in amorphous form, in combination with a hydrophilic binder and a water-soluble diluent, wherein said film is made by a process comprising: (a) dissolving donepezil hydrochloride Form I in a film forming base and liquid solvent to form a liquid intermediate; (b) spreading said liquid intermediate on a flat surface; and (c) evaporating said liquid solvent from said liquid intermediate to form said final film product.

Another preferred pharmaceutically active agent is ondansetron, preferably as its base. Ondansetron is chemically known as (±) 1,2,3,9 tetrahydro-9-methyl-3-[(2-methyl-1H-imidazol-1-yl)methyl]-4H-carbazol-4-one, and its base is represented by the following chemical structure:

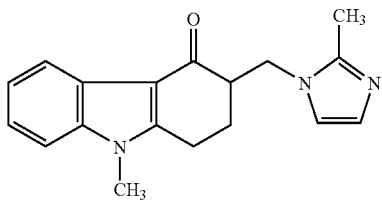 [SMILES: Cc1nccn1CC1CCc2c(c3ccccc3n2C)C1=O]

Therefore, in another embodiment the invention provides an ondansetron film strip, wherein the ondansetron is preferably provided in base form to promote GI absorption of the ondansetron. The invention also provides a non-mucoadhesive orally disintegrating film, able to disintegrate upon contact with saliva in the buccal cavity within about sixty seconds, comprising (±) 1,2,3,9 tetrahydro-9-methyl-3-[(2-methyl-1H-imidazol-1-yl)methyl]-4H-carbazol-4-one (ondansetron), in combination with a hydrophilic binder and a water-soluble diluent, and means for promoting gastrointestinal absorption of said ondansetron, wherein: (a) said means for promoting gastrointestinal absorption comprises ondansetron in base form; (b) said film comprises from about 4 to about 24 mg of ondansetron base; (c) ondansetron base is present in an amount from about 0.05% to about 50% (w/w), based on the total weight of the formulation, (d) said film has a $T_{max}$ of from about 1.5 to about 2.5 hours, and (e) said ondansetron base has an absolute bioavailability in said dosage form of from about 45% to about 75%. The film most preferably contains 4 or 8 mg of ondansetron base, and is preferably formulated according to the general formulation techniques described in this document.

Figure 4:
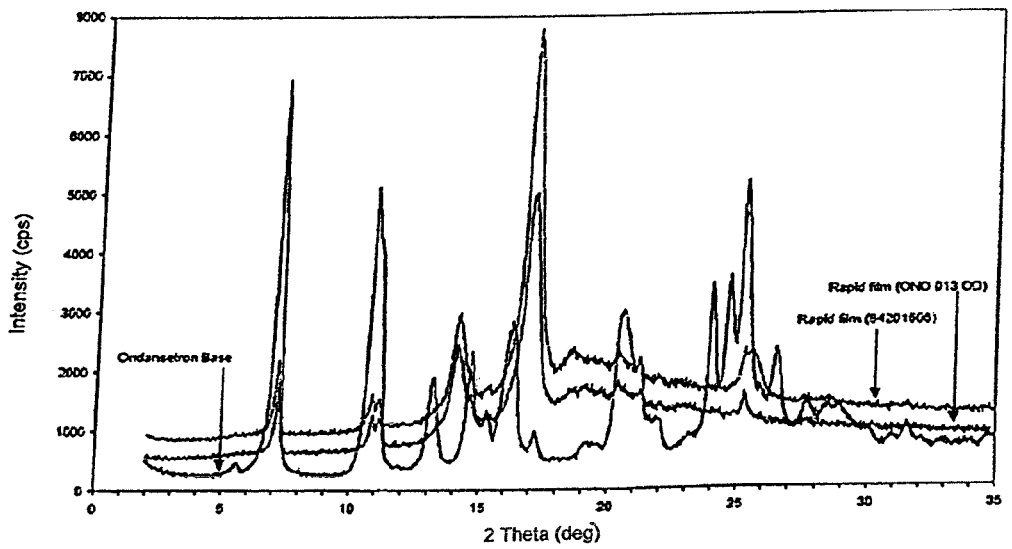
FIG. 4 is a stacking x-ray diffraction pattern for three samples—(1) ondansetron base Form B polymorph, (2) RapidFilm comprising 4 mg of ondansetron having the formulation of Table 4 and stored at 40° C., and (3) RapidFilm comprising 4 mg of ondansetron having the formulation of Table 4 (OND 013 OD), and stored at 60° C. (84201506).

It is known that ondansetron can exist in several polymorphic forms, including Forms A, B, C, D and E. See WO 03/093260 and WO 2005/080381. It has been unexpectedly found that the crystalline purity of the ondansetron in the final product influences the physical properties of the final film, and that highly pure form B is particularly preferred. In particular, for films stored at higher temperatures 60° C., physical changes in the RapidFilm have been detected, including added rigidity, warps and folding, and these changes are associated with a decrease in peak intensity and decreased purity of Form B. See FIG. 4 (where OND 013 OD refers to a RapidFilm product stored at 40° C., and 84201506 refers to the same formulation stored at 60° C.).

Therefore, in yet another embodiment, the film comprises form B polymorph that is essentially free of other polymorphic forms, i.e. greater than 70, 80, 90, 95, 98 or even 99% pure. Form B can be evaluated by X-ray diffraction as described more particularly in Example 8. Alternatively or in addition, the product is characterized by a melting endotherm at 244±2° C. when subjected to differential scanning calorimetry.

In another embodiment, the invention provides methods of using the ondansetron film strips of the present invention, for the treatment or prevention of emesis, including emesis resulting from postoperative nausea and vomiting, chemotherapy induced nausea and vomiting, and radiation induced nausea and vomiting. Therefore, the invention also provides a method of treating or preventing emesis in a human patient comprising administering to the tongue of said patient, preferably from one to three times daily, an ondansetron film strip of the present invention that contains from about 4 to about 24 mg of ondansetron base, preferably 4 or 8 mg of ondansetron base. The method is preferably practiced with an additional step that promotes gastrointestinal absorption of said ondansetron, such as swallowing said film within about sixty seconds of said administration, with or without water.

Another preferred pharmaceutically active agent is desloratadine, chemically known as 8-chloro, 6,11-dihydro-11-(4-piperdinylidene)-5H-benzo[5,6]cyclohepta[1,2-b]pyridine, and has the following chemical structure:

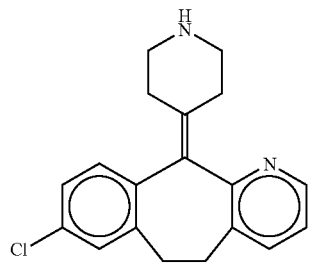

Yet another preferred pharmaceutically active agent is olanzapine, chemically known as 2-methyl-4-(4-methyl-1-piperazinyl)-10H-thieno[2,3-b][1,5]benzodiazepine, and has the following chemical structure:

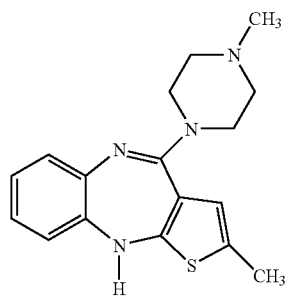 [SMILES: Cc1cc2c(s1)Nc1ccccc1N=C2N1CCN(C)CC1]

The amount of pharmaceutically active agent that can be used in the films is dependent upon the dose needed to provide an effective amount of the pharmaceutically active agent. Examples of doses for specific pharmaceutically active agents that can be delivered per one strip of rapidly dissolving oral film are reviewed in Table A, along with preferred dosing schedules and pharmacokinetic parameters. Reported pharmacokinetic data is obtained preferably in the fasted state, unless otherwise stated. Pharmacokinetic profiles by which the formulations of the present invention can be measured include AUC (0-∞ or 0-48), $T_{max}$, $C_{max}$, and combinations thereof.

The drugs can also be characterized by their solubility in water at pH 1.2, pH 4.0, or pH 6.8, or a combination of pH levels. In particular, the drug may be characterized according to any of the following solubility descriptions, as taken from USP 28/NF 23 (2005):

| Descriptive Term | Parts of Solvent Required for 1 Part of Solute |
|---|---|
| Very Soluble | Less than 1 |
| Freely Soluble | From 1 to 10 |
| Soluble | From 10 to 30 |
| Sparingly Soluble | From 30 to 100 |
| Slightly Soluble | From 100 to 1000 |
| Very Slightly Soluble | From 1000 to 10,000 |
| Practically Insoluble, or Insoluble | Greater than or equal to 10,000 |

Particular pharmacokinetic profiles of drugs of interest are set forth below in Table A.

TABLE A

| Pharmaceutical Agent | Preferred Dose | Preferred Dosing Schedule | Preferred Pharmacokinetic Parameters |
|---|---|---|---|
| Donepezil HCl (Aricept ®) | 5 mg<br>10 mg | Once Daily | Absolute Bioavailability = ca. 100%<br>$T_{max}$ = 3-4 Hours<br>Linear Pharmacokinetics over 1-10 mg dose range given once daily<br>Neither food nor time of administration influences the rate or extent of absorption |
| Ondansetron Base (Zofran ®) | 4 mg<br>8 mg<br>24 mg | 1-3 Times Daily, Not To Exceed 24 mg Per Day | Bioavailability in Healthy Subjects = ca. 45-75% (56% for 8 mg tablet)<br>$T_{max}$ = 1.5-2.5 Hours<br>Plasma concentrations are not dose proportionate<br>Bioavailability slightly enhanced by food |
| Desloratadine (Clarinex ®) | 2.5 mg<br>5.0 mg | Once Daily | $T_{max}$ = 3.0 hours*<br>Mean Steady State Peak Plasma Conc. = 4 ng/ml*<br>AUC = 56.9 ng hr/ml*<br>Food has no effect on $C_{max}$ or AUC |
| Loratadine (Claritin ®) | 10.0 mg | 10 mg per day | |
| Cetirizine Hydrochloride (Zyrtec ®) | 5.0 mg<br>10.0 mg | 5-10 mg either once or twice daily | $T_{max}$ = 1.0 hr. (fasted)<br>$C_{max}$ = 311 ng/ml when 10 mg tablet administered once daily for ten days<br>Food delays $T_{max}$ by 1.7 hrs. and decreases $C_{max}$ by 23% |
| Olanzapine (Zyprexa ®) | 2.5 mg<br>5.0 mg<br>7.5 mg<br>10.0 mg<br>15.0 mg<br>20.0 mg | 5-20 mg/day | $T_{max}$ = 6.0 hours<br>Absolute Bioavailability = ca. 60%<br>Linear pharmacokinetics over clinical dosing range<br>Food does not affect the rate or extent of absorption.<br>Administration once daily → steady state conc. ca. twice the conc. after single doses |
| Risperidone (Risperdal ®) | 0.25 mg<br>0.50 mg<br>1.0 mg<br>2.0 mg<br>3.0 mg<br>4.0 mg | 0.25-4.0 mg BID or QD | Absolute Bioavailability = ca. 70% (CV = 25%)<br>$T_{max}$ = 1.0 hour<br>Food does not affect the rate or extent of absorption. |
| Rivastigmine Tartrate (Exelon ®) | 1.5 mg<br>3.0 mg<br>4.5 mg<br>6.0 mg | 3-12 mg/day (1.5-6 mg BID) | Absolute Bioavailability = ca. 36% for 3.0 mg dose<br>$T_{max}$ = 1.0 hours (fasted state)<br>Administration with food → delays absorption ($T_{max}$) by 90 minutes; lowers $C_{max}$ by ca. 30%; and increases AUC by ca. 30%<br>Linear pharmokinetics up to 3 mg BID<br>Doubling dose from 3 to 6 mg BID → three fold increase in AUC |
| Sildenafil Citrate | 25.0 mg** | | $T_{max}$ = 30-120 minutes (60 min. median) (fasted) |

TABLE A-continued

| Pharmaceutical Agent | Preferred Dose | Preferred Dosing Schedule | Preferred Pharmacokinetic Parameters |
|---|---|---|---|
| (Viagra ®) | 50.0 mg** <br> 100.0 mg** | | $C_{max}$ = ca. 450 ng/ml.(fasted) (100 mg dose) <br> Administration with high fat meal → delays absorption ($T_{max}$) by 60 minutes; lowers $C_{max}$ by ca. 29% <br> Absolute bioavailability = ca. 40% <br> Dose proportional pharmacokinetics |
| Vardenafil HCl (Levitra ®) | 2.5 mg <br> 5.0 mg <br> 10.0 mg <br> 20.0 mg | | Absolute bioavailability = ca. 15% <br> $T_{max}$ = 30-120 minutes (60 min. median) (fasted) <br> Administration with high fat meal → lowers $C_{max}$ by ca. 18-50% <br> $C_{max}$ = ca. 10-25 ug/L (ca. 18 ug/L median) (fasted) (20 mg dose) <br> Dose proportional pharmacokinetics |
| Galantamine HBr (Razadyne ®) | 4.0 mg** <br> 8.0 mg** <br> 12.0 mg** | 8-16 mg BID | Absolute bioavailability − = ca. 90% <br> Dose proportional pharmacokinetics from 8-32 mg/day <br> $T_{max}$ = ca. 60 minutes (fasted) <br> Administration with food → delays absorption ($T_{max}$) by 90 minutes; lowers $C_{max}$ by ca. 25%; no change in AUC |
| Diclofenac K | 12.5 mg | | |
| Buprenorphine HCl (Subutex ®) | 2.0 mg** <br> 8.0 mg** | 12-16 mg/day | $AUC_{0.48}$ (hr · ng/ml) = 32.63 (CV = 25) (16.0 mg) <br> Similar plasma concentrations of buprenorphone as Suboxone ® <br> $C_{max}$ = 5.47 ng/ml (CV = 23) (16 mg) <br> Dose proportional pharmacokinetics for buprenorphine from 4-16 mg/day <br> 1.0, 2.0 and 4.0 mg doses deliver buprenorphine below limit of quantitation (0.05 ng/ml) after two hours in seven of eight subjects |
| Buprenorphine HCl/naloxone HCl dihydrate (Suboxone ®) | 2.0/0.5 mg** <br> 8.0/2.0 mg** | 12-16 mg/day | $AUC_{0.48}$ (hr.ng/ml) = 12.52 (CV = 35)(4 mg); 20.22 (CV = 43)(8 mg); 34.89 (CV = 33)(16 mg) <br> $C_{max}$ (ng/ml) = 1.84 (CV = 39) (4 mg); 3.0 (CV = 51)(8 mg); 5.95 (CV = 38) (16 mg) <br> Dose proportional pharmacokinetics for buprenorphine from 4-16 mg/day <br> 1.0, 2.0 and 4.0 mg doses deliver buprenorphine below limit of quantitation (0.05 ng/ml) after two hours in seven of eight subjects <br> Mean peak naloxone levels range from 0.11 to 0.28 ng/ml in dose range of 1-4 mg |
| Alprazolam (Xanax ®) | 0.25 mg <br> 0.5 mg <br> 1.0 mg <br> 2.0 mg | 1, 2, 3, 4, 5, 6, 7, 8, 9, or 10 mg/day, in divided doses (2, 3 or 4 doses/day) | $T_{max}$ = 1-2 hours <br> $C_{max}$ = 8.0-37 ng/ml over 0.3-3.0 mg dose range <br> Plasma levels proportionate to dose given |
| Clonazepam (Klonopin ®) | 0.125 mg <br> 0.25 mg <br> 0.5 mg <br> 1.0 mg <br> 2.0 mg | 0.25-4 mg/day in divided doses (2, 3 or 4 doses/day) | Absolute bioavailability = ca. 90% <br> $T_{max}$ = 1-4 hours |
| Diazepam (Valium ®) | 2.0 mg <br> 5.0 mg <br> 10.0 mg | 2.0-10.0 mg/dose, 2-4 times daily | $T_{max}$ = 30-90 minutes |
| Lorazepam (Ativan ®) | 0.5 mg <br> 1.0 mg <br> 2.0 mg | 1-10, 2-6 or 2-3 mg/day (1, 2, 3 or 4 doses/day) | Absolute bioavailability = ca. 90% <br> $T_{max}$ = ca. 120 minutes <br> $C_{max}$ = 20 ng/ml (2 mg); dose proportionate among doses |
| Sumatriptan Succinate (Imitrex ®) | 25.0 mg** <br> 50.0 mg** <br> 100.0 mg** | One tablet, not to exceed one tablet per hour | $C_{max}$ = 18 ng/ml (range 7-47 ng/ml) (25 mg); 51 ng/ml (range 28-100 ng/ml) (100 mg) <br> Absolute bioavailability = ca. 15% <br> $C_{max}$ is same during a migraine attack and when migraine free <br> $T_{max}$ = ca. 2.5 hrs. during attack; ca. 2.0 hrs. when migraine free <br> Single dose → dose proportionality in extent of absorption (AUC) over dose range of 25-200 mg, but $C_{max}$ is ca. 25% less than expected from 25 mg dose <br> High fat meal (100 mg tablets) → Cmax and AUC increased by 15% and 12%, respectively |

*following oral administration of 5 mg once daily for 10 days to normal healthy volunteers
**base eq.

The anti-migraine class of drugs known as triptans is especially suited for use in the dosage forms of the present invention. Sumatriptan (Imitrex®) is chemically designated as 3-[2-(dimethylamino)ethyl]-N-methyl-indole-5-methanesulfonamide. The succinic acid salt of sumatriptan is represented by the following chemical structure:

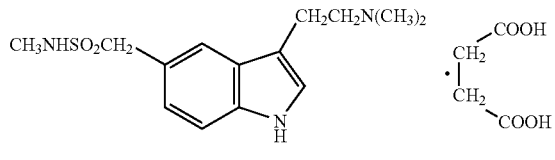

For purposes of this invention, sumatriptan can be administered as any pharmaceutically acceptable salt that demonstrates adequate stability upon storage and bioavailability upon administration, but a preferred form of sumatriptan for purposes of this invention is sumatriptan succinate (1:1).

The dosage form preferably comprises from about 15 mg to about 125 mg of sumatriptan (based on the weight of the base, in whatever form the sumatriptan is present), and more preferably comprises from about 25 mg to about 100 mg of sumatriptan, or about 25 mg, 50 mg or 100 mg specifically, of sumatriptan (corresponding to 35, 70 or 140 mg of sumatriptan succinate). The mean maximum concentration following oral dosing with 25 mg is preferably about 18 ng/mL. (with a preferred range of from about 7 to about 47 ng/mL), and 51 ng/mL (range, 28 to 100 ng/mL) following oral dosing with 100 mg of sumatriptan. In addition, the dosage form preferably yields a $T_{max}$ for the sumatriptan of from about 1.5 to about 3.0 hours, preferably from about 2.0 to about 2.5 hours, whether determined during a migraine-free period or during an attack.

Eletriptan (Relpax®) is chemically designated as (R)-3-[(1-Methyl-2-pyrrolidinyl)methyl]-5-[2-(phenylsulfonyl)ethyl]-1H-indole, and the hydrobromide salt is represented by the following chemical structure:

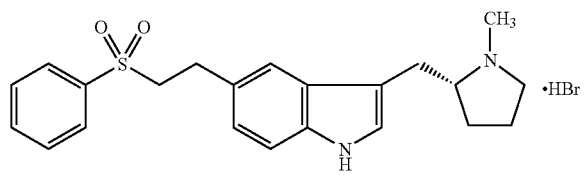 [SMILES: CN1CCC[C@@H]1Cc1c[nH]c2ccc(CCS(=O)(=O)c3ccccc3)cc12 ; Br]

For purposes of this invention, eletriptan can be administered as any pharmaceutically acceptable salt that demonstrates adequate stability upon storage and bioavailability upon administration, but a preferred form of eletriptan for purposes of this invention is eletriptan monohydrobromide.

The dosage form preferably comprises from about 10 mg to about 100 mg of eletriptan (based on the weight of the base, in whatever form the eletriptan is present), and more preferably comprises from about 10 mg to about 60 mg of eletriptan, from about 20 to about 40 mg of eletriptan, or about 20 mg or about 40 mg specifically, of eletriptan (corresponding to 24.2 mg or 48.5 mg of eletriptan hydrobromide). In addition, the dosage form preferably yields a $T_{max}$ for the eletriptan of from about 1.0 to about 3.0 hours, preferably about 1.5 to about 2.0 hours, whether determined during a migraine-free period or during an attack.

Rizatriptan (Maxalt®) is chemically described as N,N-dimethyl-5-(1H-1,2,4-triazol-1-ylmethyl)-1H-indole-3-ethanamine. The benzoic acid salt of rizatriptan is depicted by the following chemical structure:

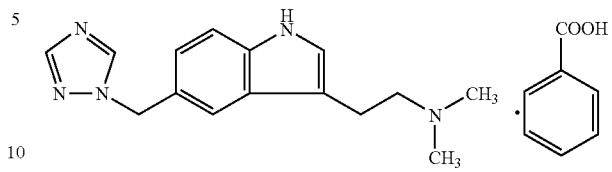

For purposes of this invention, rizatriptan can be administered as the base or as any pharmaceutically acceptable salt that demonstrates adequate stability upon storage and bioavailability upon administration, but a preferred form of rizatriptan for purposes of this invention is rizatriptan benzoate.

The dosage form preferably comprises from about 2.5 mg to about 15 mg of rizatriptan (based on the weight of the base, in whatever form the rizatriptan is present), and more preferably comprises from about 5 mg to about 10 mg of rizatriptan, or about 5 mg or about 10 mg specifically, of rizatriptan (corresponding to 7.265 or 14.53 mg of rizatriptan benzoate). In addition, the dosage form preferably yields a $t_{max}$ for the rizatriptan of from about 0.5 to about 3.0 hours, preferably from about 1.0 to about 2.5 hours, whether determined during a migraine-free period or during an attack.

Other $5\text{-HT}_{1B/1D}$ receptor agonists with which the invention could be practiced include Zolmitriptan (Zomig®), Naratriptan (Amerge®), Almotriptan (Axert®), and Frovatriptan (Frova®). Other migraine products that could be combined with the diclofenac potassium in the dosage forms of the present invention include dihydroergotamine and metoclopramide.

Zolmitriptan is chemically designated as (S)-(4)-[[3-[2-(dimethylamino)ethyl]-1H-indol-5yl]methyl]-2-oxazolidinone, and has the following chemical structure:

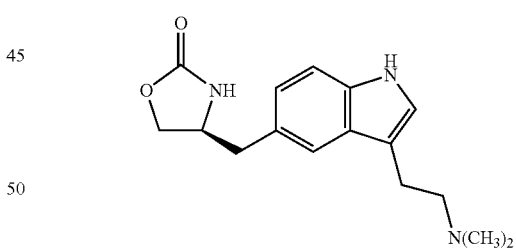

The dosage form preferably comprises from about 1.5 mg to about 7.5 mg of zolmitriptan, and more preferably comprises from about 2.5 mg to about 5.0 mg of zolmitriptan, or about 2.5 mg or about 5.0 mg specifically, of zolmitriptan. In addition, the dosage form preferably yields a $T_{max}$ for the zolmitriptan of from about 1.0 to about 4.0 hours, preferably from about 1.0 to about 2.0 hours, or from about 2.5 to about 3.5 hours, whether determined during a migraine-free period or during an attack.

Naratriptan is chemically designated as N-methyl-3-(1-methyl-4-piperidinyl)-1H-indole-5-ethanesulfonamide, and has the following chemical structure when present as the hydrochloride:

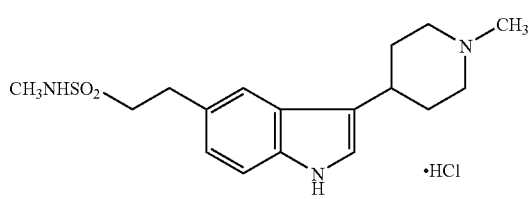

For purposes of this invention, naratriptan can be administered as the base or as any pharmaceutically acceptable salt that demonstrates adequate stability upon storage and bioavailability upon administration, but a preferred form of naratriptan for purposes of this invention is naratriptan hydrochloride.

The dosage form preferably comprises from about 0.5 mg to about 5.0 mg of naratriptan (based on the weight of the base, in whatever form the naratriptan is present), and more preferably comprises from about 1.0 mg to about 2.5 mg of naratriptan, or about 1.0 mg or about 2.5 mg specifically, of naratriptan (corresponding to 1.11 or 2.78 mg of naratriptan hydrochloride). In addition, the dosage form preferably yields a $t_{max}$ for the naratriptan of from about 1.5 to about 4.5 hours, preferably from about 2.0 to about 4.0 hours, whether determined during a migraine-free period or during an attack.

Almotriptan malate is chemically designated as 1-[[[3-[2-(dimethylamino)ethyl]-1H-indol-5-yl]methyl]sulfonyl]pyrrolidine (±)-hydroxybutanedioate (1:1), and has the following chemical structure when present as the malate:

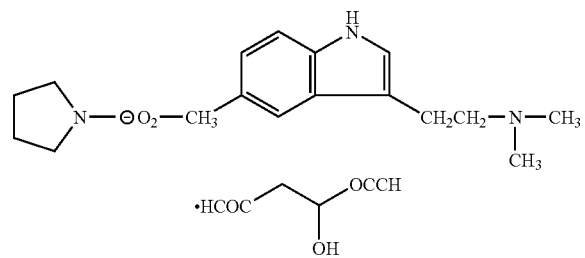

For purposes of this invention, almotriptan can be administered as the base or as any pharmaceutically acceptable salt that demonstrates adequate stability upon storage and bioavailability upon administration, but a preferred form of almotriptan for purposes of this invention is almotriptan malate.

The dosage form preferably comprises from about 2.5 mg to about 15.0 mg of almotriptan (based on the weight of the base, in whatever form the almotriptan is present), and more preferably comprises from about 6.25 mg to about 12.5 mg of almotriptan, or about 6.25 mg or about 12.5 mg specifically, of almotriptan. In addition, the dosage form preferably yields a $T_{max}$ for the almotriptan of from about 0.5 to about 4.0 hours, preferably from about 1.0 to about 3.0 hours, whether determined during a migraine-free period or during an attack.

Frovatriptan is preferably administered as the succinic acid salt, in an amount of from about 1.0 to about 5.0 mg, preferably about 2.5 mg (based on the weight of frovatriptan). In addition, the dosage form preferably yields a $T_{max}$ for the frovatriptan of from about 0.5 to about 4.0 hours, whether determined during a migraine-free period or during an attack.

Other Pharmaceutically Active Agents

The expression "pharmaceutically active agents" as used herein is intended to encompass agents other than foods, which promote a structural and/or functional change in and/or on bodies to which they have been administered. These agents are not particularly limited; however, they should be physiologically acceptable and compatible with the film.

Suitable pharmaceutically active agents include, but are not limited to:

antimicrobial agents, such as triclosan, cetyl pyridium chloride, domiphen bromide, quaternary ammonium salts, zinc compounds, sanguinarine, fluorides, alexidine, octonidine, EDTA, and the like;

non-steroidal anti-inflammatory drugs, such as aspirin, acetaminophen, ibuprofen, ketoprofen, diclofenac, diflunisal, fenoprofen calcium, naproxen, tolmetin sodium, indomethacin, and the like;

anti-tussives, such as benzonatate, caramiphen edisylate, menthol, dextromethorphan hydrobromide, chlophedianol hydrochloride, and the like;

decongestants, such as pseudoephedrine hydrochloride, phenylepherine, phenylpropanolamine, pseudoephedrine sulfate, and the like;

anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like;

expectorants, such as guaifenesin, ipecac, potassium iodide, terpin hydrate, and the like;

anti-diarrheals, such as loperamide, and the like;

$H_2$-antagonists, such as famotidine, ranitidine, and the like;

proton pump inhibitors, such as omeprazole, lansoprazole, and the like;

general nonselective CNS depressants, such as aliphatic alcohols, barbiturates and the like;

general nonselective CNS stimulants such as caffeine, nicotine, strychnine, picrotoxin, pentylenetetrazol and the like;

drugs that selectively modify CNS function, such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like;

antiparkinsonism drugs such as levodopa, amantadine and the like;

narcotic-analgesics such as morphine, heroin, hydromorphone, metopon, oxymorphone, levorphanol, codeine, hydrocodone, xycodone, nalorphine, naloxone, naltrexone and the like;

analgesic-antipyretics such as salycilates, phenylbutazone, indomethacin, phenacetin and the like; and psychopharmacological drugs such as chlorpromazine, methotrimeprazine, haloperidol, clozapine, reserpine, imipramine, tranylcypromine, phenelzine, lithium and the like.

Other suitable drugs include ambroxol hydrochloride, apomorphine, ascorbic acid, betamethasone, caffeine, dextromethorphan, glimepiride, hydrocortisone, ketotifen, loperamide, meclozine, melatonin, neramexane, piroxicam, sodium picosulfate, and zinc histidine, and pharmaceutically acceptable salts thereof.

The most preferable drugs are those in which a unitary dosage form comprises no more than about 50 mg, 25 mg, 15 mg or 10 mg of the active ingredient per unit.

Dispensing/Packaging Format

The films of the present invention can be provided in various dispensing and/or packaging configurations. For example, in one embodiment, the films would be packaged in a dose card that contains a plurality of individually wrapped films protected by moisture impermeable removable laminar covers. Examples of suitable dose cards are reported, for example, in U.S. Pat. No. 6,520,329, WO 2006/056161, WO 02/059012, EP 1 353 857, and WO 01/62621, the disclosures of which are hereby incorporated by reference.

In another embodiment, the films would be packaged in a hermetically sealed, moisture impermeable flat pouch comprising two walls adhered around the edges. In a preferred embodiment, the packaging prevents the dosage form from absorbing more than 4.0, 3.0, 2.0 or even 1.0 wt. % moisture in three months when stored at 40° C. and 75% relative humidity.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at room temperature, and pressure is at or near atmospheric.

Example 1

Representative Ondansetron Formulation

Table 1 depicts a representative film formulation that contains 8.0 mg of ondansetron as its base, in order to promote gastrointestinal absorption.

TABLE 1

Representative Formulation of Ondansetron Base Film Dosage Form

| Pos. | Ingredient | Amount per Film [mg] | Amount per Film [%] |
|---|---|---|---|
| 1 | Ondansetron (as base) | 8.0 | 15.84 |
| 2 | Mowiol (Polyvinylalcohol) | 22.0 | 43.56 |
| 3 | PEG (polyethylene glycol) | 6.0 | 11.88 |
| 4 | Glycerol anhydrous | 2.0 | 3.96 |

TABLE 1-continued

Representative Formulation of Ondansetron Base Film Dosage Form

| Pos. | Ingredient | Amount per Film [mg] | Amount per Film [%] |
|---|---|---|---|
| 5 | Rice Starch | 10.0 | 19.80 |
| 6 | Acesulfam K | 0.2 | 0.40 |
| 7 | Titanium dioxide | 0.3 | 0.59 |
| 8 | Menthol | 1.0 | 1.98 |
| 9 | Polysorbate | 1.0 | 1.98 |
|  | TOTAL | 50.5 | 100.0 |

Example 1A

Comparative Bioavailability of Zofran® Brand Tablets

Tables 2 and 3 present clinical pharmacokinetic data for Zofran® brand immediate release 8 mg and 24 mg tablets, as reported in the Food and Drug Administration (FDA) approved prescribing information for this product:

TABLE 2

Pharmacokinetics in Normal Volunteers Single 8 mg Zofran ® Tablet Dose

| Age-group (years) | | Mean Weight (kg) | n | Peak Plasma Concentration (ng/mL) | Time of Peak Plasma Concentration (h) | Mean Elimination Half-life (h) | Systemic Plasma Clearance L/h/kg | Absolute Bioavailability |
|---|---|---|---|---|---|---|---|---|
| 18-40 | M | 69.0 | 6 | 26.2 | 2.0 | 3.1 | 0.403 | 0.483 |
|  | F | 62.7 | 5 | 42.7 | 1.7 | 3.5 | 0.354 | 0.663 |
| 61-74 | M | 77.5 | 6 | 24.1 | 2.1 | 4.1 | 0.384 | 0.585 |
|  | F | 60.2 | 6 | 52.4 | 1.9 | 4.9 | 0.255 | 0.643 |
| ≥75 | M | 78.0 | 5 | 37.0 | 2.2 | 4.5 | 0.277 | 0.619 |
|  | F | 67.6 | 6 | 46.1 | 2.1 | 6.2 | 0.249 | 0.747 |

TABLE 3

Pharmacokinetics in Normal Volunteers Single 24 mg Zofran ® Tablet Dose

| Age-group (years) | | Mean Weight (kg) | n | Peak Plasma Concentration (ng/mL) | Time of Peak Plasma Concentration (h) | Mean Elimination Half-life (h) |
|---|---|---|---|---|---|---|
| 18-43 | M | 84.1 | 8 | 125.8 | 1.9 | 4.7 |
|  | F | 71.8 | 8 | 194.4 | 1.6 | 5.8 |

Example 2

Comparative Ondansetron Dissolution Study

Dissolution studies were conducted on five different orally administered ondansetron products: Zofran®4 mg Zydis® Lingual; Zofran® 8 mg Zydis® Lingual; ondansetron 4 mg RapidFilm having the formulation of Table 4; ondansetron 8 mg RapidFilm having the formulation of Table 4 (punched in 6 cm² rectangles); and Zofran® 8 mg Filmtablet.

TABLE 4

Ondansetron RapidFilm Formulation

| Ingredients | Master Batch Formula [g/100 g] | Formula dosage form [mg/unit] [3.00 cm³ final film] |
|---|---|---|
| Ondansetron Base | 6.8116 | 4.000 |
| Polyvinylalcohol 4-88 | 18.7321 | 11.000 |
| PEG 1000 | 5.1088 | 3.000 |
| Glycerol anhydr. | 1.7032 | 1.000 |
| Rice starch | 8.5149 | 5.000 |
| Acesulfam K | 0.1707 | 0.100 |
| Titanium dioxide | 0.2559 | 0.150 |
| Levomenthol | 0.8514 | 0.500 |
| Polysorbate 80 | 0.8514 | 0.500 |
| Ethanol 96% | 23.7519 | Removed |
| Purified Water | 33.2481 | Removed |

Dissolution studies were performed according to Ph. Eur. 2.9.4, paddle, sinker, 900 ml, using 0.1N HCl buffered water at pH 1.0. Stirring occurred at 100 rpm and 37° C. Relative pharmacokinetics are reported in Table 5 below and FIG. 1.

TABLE 5

| Lot Time [min] | 5G033 Zofran 8 mg Film tablet [%] | R208046 Zofran 8 mg Zydis Lingual [%] | OND008OD_8 mg Ondanaetron 8 mg Rapid Film [%] | 5H010 Zofran 4 mg Zydia Lingual [%] | OND008OD_4 mg Ondanaetron 4 mg Rapid Film [%] |
|---|---|---|---|---|---|
| 0 | 0 | 0 | 0 | 0 | 0 |
| 1 | 0.8 | 100.3 | 97.1 | 102.3 | 71.8 |
| 3 | 9 | 104.6 | 102 | 101.7 | 98.4 |
| 5 | 22.7 | 103.4 | 102.4 | 101.4 | 103.3 |
| 7 | 63.4 | 102.1 | 101.7 | 101.3 | 105 |
| 10 | 103.3 | 100.8 | 100.8 | 101.8 | 105.2 |

Example 3

Comparative Ondansetron Bioavailability Study

A clinical study was conducted to compare the bioavailability profile and the pharmacokinetic parameters of two medicinal products containing 8 mg ondansetron: (1) ondansetron RapidFilm formulated having the formulation reported in Table 4, and (2) Zofran®8 mg. Zydis Lingual-Orally Disintegrating Tablets.

The study was a randomized, single dose, two way, two sequence crossover, open label with seven days washout period study under fasting conditions. Orally disintegrating tablet and RapidFilm was allowed to dissolve in the subject's mouth for about 10 seconds before the patient was asked to swallow. The study included 7 healthy adult Caucasian males.

Figure 2A:
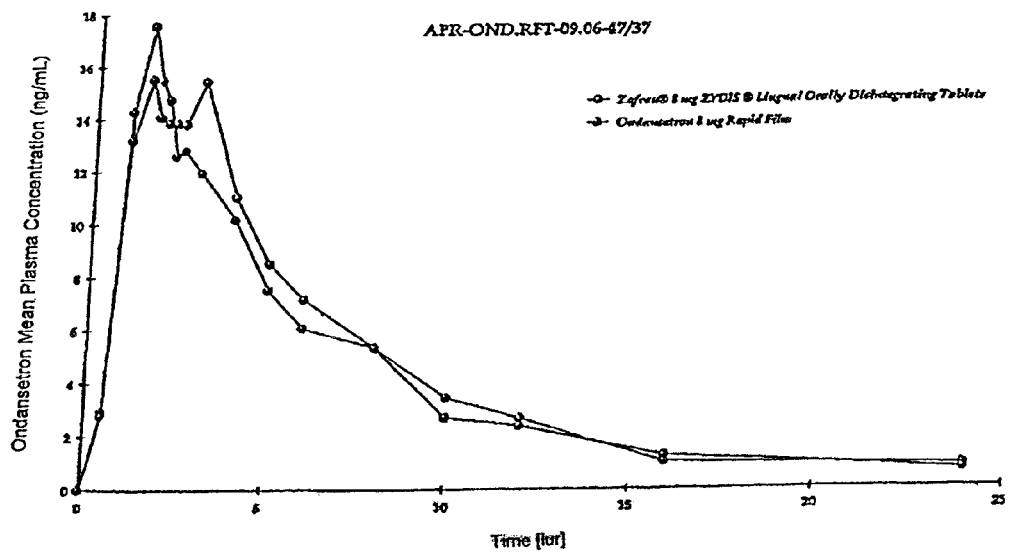
FIG. 2 depicts mean (FIG. 2A) and log mean (FIG. 2B) drug plasma concentration profiles versus time for 8 mg ondansetron RapidFilm investigational product versus Zofran® 8 mg Lingual orally disintegrating tablets, as described in Table 6.
Figure 2B:
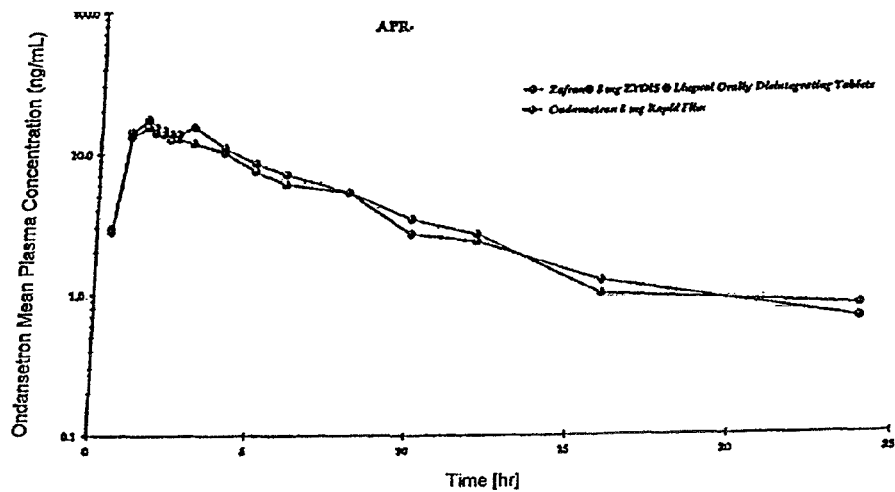

Table 6 reports pharmacokinetic and bioequivalence parameters observed during the study. FIG. 1 is a comparison of dissolution profiles over time comparing three commercially available formulations of ondansetron with two ondansetron RapidFilm formulations, as described in Table 4. FIG. 2 depicts mean (FIG. 2A) and log mean (FIG. 2B) drug plasma concentration profiles versus time for 8 mg ondansetron RapidFilm investigational product (Table 4) versus Zofran®8 mg. Lingual orally disintegrating tablets.

TABLE 6

| Pharmacokinetic Parameter | Investigational Product (Algebraic Mean ± SD) | Reference Product (Algebraic Mean ± SD) |
|---|---|---|
| $C_{max}$ (ng/ml) | 18.75 ± 6.262 | 20.37 ± 6.470 |
| $AUC_{0-t}$ (ng * hr/ml) | 94.11 ± 38.078 | 100.05 ± 48.826 |
| $AUC_{0-\infty}$ (ng * hr/ml) | 98.18 ± 39.345 | 103.66 ± 49.691 |
| $T_{max}$ (hr) | 1.58 ± 0.408 | 1.71 ± 0.749 |
| $T_{lag}$ (hr) | 0.08 ± 0.204 | 0.08 ± 0.204 |
| $T_{1/2}$ (hr) | 3.45 ± 0.817 | 3.62 ± 0.624 |
| $K_{elimination}$ (hr$^{-1}$) | 0.2111 ± 0.05284 | 0.1965 ± 0.03480 |
| $(AUC_{0-t}/AUC_{0-\infty})$ % | 95.67 ± 1.467 | 96.14 ± 1.362 |

| BE Assessment Parameter | $C_{max}$ (80.00-125.00) | $AUC_{0-t}$ (80.00-125.00) | $AUC_{0-\infty}$ (80.00-125.00) |
|---|---|---|---|
| Point Estimate (%) | 91.84 | 96.32 | 96.79 |
| Lower Limit (%) | 72.64 | 82.87 | 83.81 |
| Upper Limit (%) | 116.13 | 111.96 | 111.78 |
| Prob < 80.00 | 0.1389 | 0.0291 | 0.0239 |
| Prob > 125.00 | 0.0244 | 0.0105 | 0.0096 |

Example 4

Representative Donepezil Formulations

Table 7 recites the ingredients of a film formulation that contains 10.0 mg of donepezil hydrochloride. The formulation lacks any special ingredients for promoting GI absorption, other than the formulation's affinity for water, and its rapid disintegration in saliva. Table 5 describes an alternative formulation of 10.0 mg donepezil hydrochloride that contains cyclodextrin to retard the absorption of active ingredient through the oral mucosa, and thereby promote GI absorption.

TABLE 7

Representative Formulation of Donepezil HCl Orally Disintegrating Film

| Pos. | Ingredient | Amount per Film [mg] | Amount per Film [%] |
|---|---|---|---|
| 1 | Donepezil HCl | 10.00 | 12.27 |
| 2 | Polyethylenoxide | 50.00 | 61.36 |
| 3 | Polysorbate 80 (Tween 80) | 1.00 | 1.23 |
| 4 | Glycerol anhydrous | 12.00 | 14.73 |
| 5 | Citric acid anhydrous | 1.00 | 1.23 |
| 6 | Titanium dioxide | 0.50 | 0.61 |
| 7 | Acesulfam K | 1.50 | 1.84 |
| 8 | Anis flavor | 1.65 | 2.02 |
| 9 | Peppermint flavour | 3.84 | 4.71 |
| | TOTAL | 81.49 | 100.0 |

TABLE 8

Alternative Representative Formulation of Donepezil HCl Orally Disintegrating Film

| Pos. | Ingredient | Amount per Film [mg] | Amount per Film [%] |
|---|---|---|---|
| 1 | Donepezil HCl | 10.0 | 9.48 |
| 2 | β-Cyclodextrin (Cavamax W7) | 44.5 | 42.18 |
| 3 | Polyvinylalkohol (Mowiol 4-88) | 30.0 | 28.44 |
| 4 | Polyethylenglycol (PEG 1000) | 8.0 | 7.58 |
| 5 | Propylenglycol | 5.0 | 4.74 |
| 6 | Citric acid anhydrous | 1.0 | 0.95 |
| 7 | Acesulfam K | 1.5 | 1.42 |
| 8 | Anis flavor | 1.65 | 1.56 |
| 9 | Peppermint flavour | 3.84 | 3.64 |
|  | TOTAL | 105.49 | 100.0 |

Example 5

Comparative Dissolution Study of Donepezil Formulations

A comparative dissolution study was undertaken to compare the dissolution profile of various RapidFilm products and formulations with commercially available donepezil products. The formulations for the donepezil film products are reported in Tables 9-14.

TABLE 9

Donepezil RapidFilm; Prototype A

| Ingredients | Master Batch Formula [g/100 g] | Formula dosage form [mg/unit] [3.00 cm³ final film] |
|---|---|---|
| Donepezil HCl (Form I) | 4.2470 | 5.000 |
| Polyvinylalcohol 4-88 | 12.7410 | 15.000 |
| PEG 1000 | 3.3970 | 4.000 |
| Acesulfam K | 0.6370 | 0.750 |
| β-Cyclodextrine | 18.8980 | 22.250 |
| Citric Acid anhyd. | 0.4250 | 0.500 |
| Propylenglycol | 2.1230 | 2.500 |
| Anis | 0.7010 | 0.825 |
| Peppermint | 1.6310 | 1.920 |
| Purified Water | 39.9000 | Removed |
| Ethanol abs. | 15.3000 | Removed |

TABLE 10

Donepezil RapidFilm; Prototype B

| Ingredients | Master Batch Formula [g/100 g] | Formula dosage form [mg/unit] [3.00 cm³ final film] |
|---|---|---|
| Donepezil HCl (Form I) | 3.0540 | 5.000 |
| Polyethylenoxide | 15.2680 | 25.000 |
| Acesulfam K | 0.4580 | 0.750 |
| Polysorbat 80 | 0.3050 | 0.500 |
| Glycerol anhydr. | 3.6640 | 6.000 |
| Titanium dioxide | 0.1530 | 0.250 |
| Citric acide monohydrate | 0.3050 | 0.500 |
| Anis | 0.5040 | 0.825 |
| Peppermint | 1.1730 | 1.920 |
| Purified Water | 15.3000 | Removed |
| Ethanol abs. | 59.8200 | Removed |

TABLE 11

Donepezil RapidFilm; Prototype C

| Ingredients | Master Batch Formula [g/100 g] | Formula dosage form [mg/unit] [3.00 cm³ final film] |
|---|---|---|
| Donepezil HCl (amorphous) | 13.7230 | 5.000 |
| Lactose | 10.2920 | 15.000 |
| Polyvinylalcohol 4-88 | 10.2920 | 15.000 |
| PEG 1000 | 2.7450 | 4.000 |
| Acesulfam K | 0.5150 | 0.750 |
| β-Cyclodextrine | 15.2660 | 22.250 |
| Citric Acid anhyd. | 0.3430 | 0.500 |
| Propylenglycol | 1.7150 | 2.500 |
| Anis | 0.5660 | 0.825 |
| Peppermint | 1.3170 | 1.920 |
| Purified Water | 41.2000 | Removed |
| Ethanol abs. | 12.4000 | Removed |

TABLE 12

Donepezil RapidFilm; Prototype E

| Ingredients | Master Batch Formula [g/100 g] | Formula dosage form [mg/unit] [3.00 cm³ final film] |
|---|---|---|
| Donepezil HCl (Form I) | 4.8799 | 5.000 |
| Polyvinylalcohol 4-88 | 13.8054 | 15.000 |
| PEG 1000 | 3.6813 | 4.000 |
| Acesulfam K | 0.6903 | 0.750 |
| β-Cyclodextrine | 11.7691 | 11.125 |
| Citric Acid anhyd. | 0.4603 | 0.500 |
| Propylenglycol | 2.3008 | 2.500 |
| Anis | 0.7783 | 0.825 |
| Peppermint | 1.8022 | 1.920 |
| Purified Water | 43.2660 | Removed |
| Ethanol 96% | 16.5664 | Removed |

TABLE 13

Donepezil/Eudragit Pre-Mix for Prototype F

| Ingredients | Master Batch Formula [g/100 g] |
|---|---|
| Donepezil HCl (Form I) | 12,5000 |
| Eudragit E PO | 12,5000 |
| Ethanol abs.*) | 75,0000 |

*not part of the finished product

TABLE 14

Donepezil/Eudragit RapidFilm; Prototype F

| Ingredients | Master Batch Formula [g/100 g] | Formula dosage form [mg/unit] [3.00 cm³ final film] |
|---|---|---|
| Donepezil HCl/Eudragit combination) | 10.0000 | 10.000 |
| Polyvinylalcohol 4-88 | 15.0000 | 15.000 |
| PEG 1000 | 4.0000 | 4.000 |
| Acesulfam K | 0.7500 | 0.750 |
| Propylenglycol | 2.5000 | 2.500 |
| Anis | 0.8250 | 0.825 |
| Peppermint | 1.9200 | 1.920 |
| Aqua purificata* | 65.0000 | Removed |

*not part of the finished product

Figure 3:
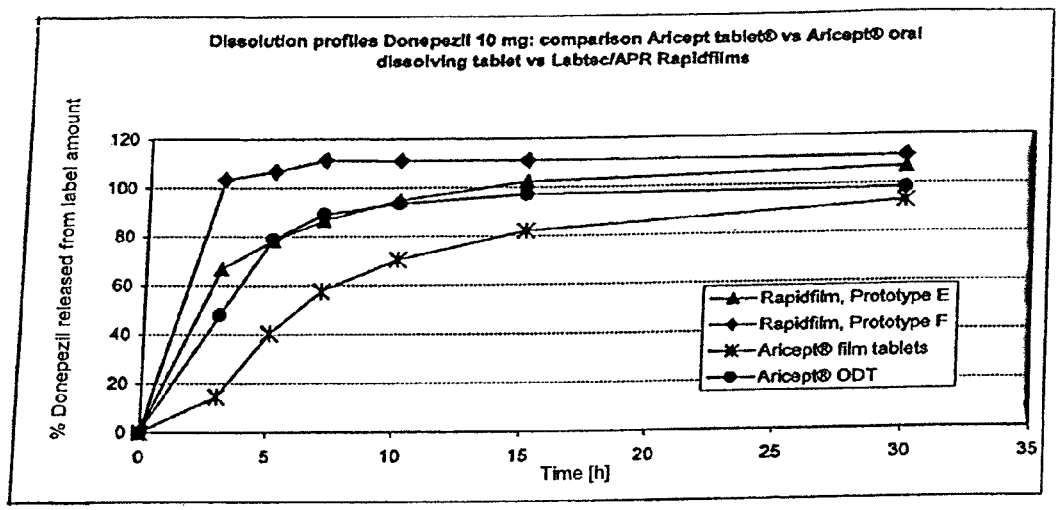
FIG. 3 is a comparison of dissolution profiles over time comparing commercially available donepezil hydrochloride immediate release tablets, commercially available donepezil hydrochloride orally disintegrating tablets, and four donepezil hydrochloride RapidFilm formulations, as described in Tables 9-14. The top line at 3 minutes is RapidFilm prototype F; the second line at 3 minutes is Aricept® film tablets; the third line at 3 minutes is RapidFilm prototype E; the fourth line at 3 minutes is RapidFilm prototype A; the fifth line at 3 minutes is Aricept® ODT; the bottom line at 3 minutes is RapidFilm prototype C.

Dissolution studies were performed according to Ph. Eur. 2.9.4, paddle, sinker, 900 ml, using 0.1N HCl buffered water at pH 1.0. Stirring occurred at 50 rpm and 37° C. Relative pharmacokinetics are reported in Table 15 below and FIG. 3.

TABLE 15

| Time [min] | Rapid film, Prototype A [%] | Rapid film, Prototype C [%] | Rapid film, Prototype E [%] | Rapid film, Prototype F [%] | Aricept film Tablets [%] | Aricept ODT [%] |
|---|---|---|---|---|---|---|
| 0 | 0 | 0 | 0 | 0 | 0 | 0 |
| 3 | 58.8 | 86.5 | 66.8 | 103.3 | 14.5 | 47.9 |
| 5 | 78.7 | 101.0 | 78.3 | 106.7 | 40.3 | 78.9 |
| 7 | 90.0 | 102.4 | 86.5 | 111.3 | 57.4 | 89.0 |
| 10 | 93.7 | 105.0 | 94.7 | 111.0 | 70.5 | 93.5 |
| 15 | 94.0 | 103.1 | 102.4 | 111.0 | 82.1 | 97.1 |
| 30 | 93.9 | 102.9 | 106.8 | 111.5 | 92.9 | 98.1 |

Example 6

Representative Diclofenac K Formulation

Table 16 recites the ingredients of a 6 cm² film formulation that contains 12.5 mg of diclofenac potassium (matrix weight=120.7 g/m²). The film contains an ion exchange resin to retard the absorption of active ingredient through the oral mucosa, and thereby promote GI absorption.

TABLE 16

Representative Formulation of Diclofenac K Orally Disintegrating Film

| Pos. | Ingredient | Amount per Film [mg] | Amount per Film [%] |
|---|---|---|---|
| 1 | Mowiol 4-88 | 22.00 | 30.4 |
| 2 | PEG 1000 | 6.00 | 8.3 |
| 3 | Neohesperidin DC | 0.60 | 0.8 |
| 4 | Duolite AP 143/1093 | 18.75 | 25.9 |
| 5 | Menthol | 1.00 | 1.4 |
| 6 | Polysorbate 80 | 1.50 | 2.1 |
| 7 | Ferrum Oxide (No. 3) | 0.05 | 0.1 |
| 8 | Rice Starch | 10.0 | 13.8 |
| 9 | Diclofenac Potassium | 12.5 | 17.3 |
|  | TOTAL | 72.40 | 100.0 |
| 10 | Ethanol 96% (v/v)* | 50.0 |  |
| 11 | Purified Water* | 70.0 |  |

*Removed by evaporation.

Example 7

Representative Formulations of Other Drugs

Tables 17-37 below present representative formulations of alternative drugs manufactured according to the present invention.

Ambroxol

Using the following components a laminate with a nominal size of 1 000.0 cm² should be obtained. From the dried laminate films with a size of 6.0 cm² were punched.

TABLE 17

| ACTIVE INGREDIENT | POLYMERS | OTHER COMPONENTS | SOLVENTS |
|---|---|---|---|
| 3.333 g Ambroxol hydrochloride | 3.667 g Poly(vinyl alcohol) 4-88 1.000 g PEG 1000 | 0.033 g Saccharin sodium 0.100 g Polysorbate 80 0.250 g | 8.3 g Ethanol 96% (V/V) 11.7 g Purified water |

TABLE 17-continued

| ACTIVE INGREDIENT | POLYMERS | OTHER COMPONENTS | SOLVENTS |
|---|---|---|---|
|  |  | Peppermint oil 0.100 g *Eucalyptus* oil 1.667 g Rice starch |  |

Apomorphine

Using the following components a laminate with a nominal size of 400.0 cm² should be obtained. From the dried laminate films with a size of 6.0 cm² were punched.

TABLE 18

| ACTIVE INGREDIENT | POLYMERS | OTHER COMPONENTS | SOLVENTS |
|---|---|---|---|
| 0.228 g Apomorphine hydrochloride | 2.000 g Poly(vinyl alcohol) 4-88 0.533 g PEG 1000 | 0.003 g Neohesperidin dihydrochalcone 0.003 g Saccharin sodium 0.033 g Peppermint oil 0.001 g Patent blue V 0.009 g Titanium dioxide | 3.3 g Ethanol 96% (V/V) 4.7 g Purified water |

Ascorbic Acid

Using the following components a laminate with a nominal size of 6 000.0 cm² should be obtained. From the dried laminate films with a size of 5.0 cm² were punched.

TABLE 19

| ACTIVE INGREDIENT | POLYMERS | OTHER COMPONENTS | SOLVENTS |
|---|---|---|---|
| 24.000 g Ascorbic acid | 24.000 g Poly(vinyl alcohol) IF 14 000 6.000 g PEG 1000 | 0.120 g Saccharin sodium 8.400 g Rice starch 0.720 g Black currant flavor 2.400 g Azorubin (Stock solution 1%) 0.420 g Titanium dioxide | 42.0 g Ethanol 96% (V/V) 60.0 g Purified water |

Betamethasone

Using the following components a laminate with a nominal size of 1 000.0 cm² should be obtained. From the dried laminate films with a size of 6.0 cm² were punched.

TABLE 20

| ACTIVE INGREDIENT | POLYMERS | OTHER COMPONENTS | SOLVENTS |
|---|---|---|---|
| 0.667 g Betamethasone | 3.667 g Poly(vinyl alcohol) 4-88<br>1.000 g PEG 1000 | 0.050 g Titanium dioxide<br>1.667 g Rice starch | 8.3 g Ethanol 96% (V/V)<br>11.7 g Purified water |

Caffeine

Using the following components a laminate with a nominal size of 1 000.0 cm² should be obtained. From the dried laminate films with a size of 6.0 cm² were punched.

TABLE 21

| ACTIVE INGREDIENT | POLYMERS | OTHER COMPONENTS | SOLVENTS |
|---|---|---|---|
| 6.667 g Caffeine | 2.833 g Hydroxypropyl-cellulose<br>0.950 g PEG 1000<br>0.717 g Povidone | 0.600 g Glycerol, anhydrous<br>0.1.250 g Citric acid, anhydrous<br>0.250 g Neohesperidin dihydrochalcone | 20.0 g Ethanol, anhydrous |

Caffeine

Using the following components a laminate with a nominal size of 4 000.0 cm² should be obtained. From the dried laminate films with a size of 6.0 cm² were punched.

TABLE 22

| ACTIVE INGREDIENT | POLYMERS | OTHER COMPONENTS | SOLVENTS |
|---|---|---|---|
| 33.333 g Caffeine | 20.000 g Poly(vinyl alcohol) 4-88<br>5.333 g PEG 1000 | 0.333 g Neohesperidin dihydrochalcone<br>0.333 g Saccharin sodium<br>3.333 g Glycerol 85% | 33.3 g Ethanol 96% (V/V)<br>46.7 g Purified water |

Dextromethorphan

Using the following components a laminate with a nominal size of 2 000.0 cm² should be obtained. From the dried laminate films with a size of 6.0 cm² were punched.

TABLE 23

| ACTIVE INGREDIENT | POLYMERS | OTHER COMPONENTS | SOLVENTS |
|---|---|---|---|
| 3.333 g Dextromethorphan | 10.000 g Poly (vinyl alcohol) 4-88<br>2.667 g PEG 1000 | 0.167 g Neohesperidin dihydrochalcone | 16.7 g Ethanol 96% (V/V)<br>22.0 g Purified water |

Diclofenac

Using the following components a laminate with a nominal size of 2 000.0 cm² should be obtained. From the dried laminate films with a size of 6.0 cm² were punched.

TABLE 24

| ACTIVE INGREDIENT | POLYMERS | OTHER COMPONENTS | SOLVENTS |
|---|---|---|---|
| 4.167 g Diclofenac potassium | 7.333 g Poly (vinyl alcohol) 4-88<br>2.000 g PEG 1000 | 0.200 g Neohesperidin<br>0.500 g Peppermint oil<br>0.367 g Sicovit (Stock solution 1%)<br>0.333 g Polysorbate 80<br>3.333 g Rice starch | 16.7 g Ethanol 96% (V/V)<br>23.3 g Purified water |

Glimepiride

Using the following components a laminate with a nominal size of 1 000.0 cm² should be obtained. From the dried laminate films with a size of 6.0 cm² were punched.

TABLE 25

| ACTIVE INGREDIENT | POLYMERS | OTHER COMPONENTS | SOLVENTS |
|---|---|---|---|
| 0.500 g Glimepiride | 5.000 g Poly (vinyl alcohol) 4-88<br>1.333 g PEG 1000 | 0.083 g Neohesperidin dihydrochalcone<br>0.033 g Menthyl pyrrolidone carboxylate<br>0.833 g Glycerol 85% | 8.300 g Ethanol 96% (V/V)<br>11.700 g Purified water |

Hydrocortisone

Using the following components a laminate with a nominal size of 1 000.0 cm² should be obtained. From the dried laminate films with a size of 6.0 cm² were punched.

TABLE 26

| ACTIVE INGREDIENT | POLYMERS | OTHER COMPONENTS | SOLVENTS |
|---|---|---|---|
| 1.867 g Hydrocortisone acetate | 3.667 g Poly (vinyl alcohol) 4-88<br>1.000 g PEG 1000 | 0.050 g Titanium dioxide<br>1.667 g Rice starch | 8.3 g Ethanol 96% (V/V)<br>11.7 g Purified water |

Ketotifen

Using the following components a laminate with a nominal size of 1 500.0 cm² should be obtained. From the dried laminate films with a size of 6.7 cm² were punched.

TABLE 27

| ACTIVE INGREDIENT | POLYMERS | OTHER COMPONENTS | SOLVENTS |
|---|---|---|---|
| 0.307 g Ketotifen fumarate | 2.226 g Poly (vinyl alcohol) 8-88<br>4.451 g Poly (vinyl alcohol) 3-83<br>0.668 g PEG 1000 | 0.111 g Polysorbate 20<br>4.451 g Rice starch | 11.128 g Ethanol 96% (V/V)<br>15.579 g Purified water |

Loperamide

Using the following components a laminate with a nominal size of 1 500.0 cm² should be obtained. From the dried laminate films with a size of 6.7 cm² were punched.

TABLE 28

| ACTIVE INGREDIENT | POLYMERS | OTHER COMPONENTS | SOLVENTS |
|---|---|---|---|
| 0.445 g Loperamide hydrochloride | 2.226 g Poly (vinyl alcohol) 8-88 4.451 g Poly (vinyl alcohol) 3-83 0.334 g PEG 1000 | 0.111 g Polysorbate 20 4.451 g Rice starch | 11.128 g Ethanol 96% (V/V) 15.579 g Purified water |

Meclozine sing the following components a laminate with a nominal size of 2 000.0 cm² should be obtained. From the dried laminate films with a size of 6.0 cm² were punched.

TABLE 29

| ACTIVE INGREDIENT | POLYMERS | OTHER COMPONENTS | SOLVENTS |
|---|---|---|---|
| 9.888 g Meclozine hydrochloride | 5.667 g Poly (vinyl alcohol) 4-88 1.500 g PEG 1000 | 0.133 g Menthol 0.133 g Licorize flavor 1.000 g Glycerol 2.500 g Rice Starch | 9.7 g Ethanol 96% (V/V) 13.3 g Purified water |

Melatonin sing the following components a laminate with a nominal size of 500.0 cm² should be obtained. From the dried laminate films with a size of 6.0 cm² were punched.

TABLE 30

| ACTIVE INGREDIENT | POLYMERS | OTHER COMPONENTS | SOLVENTS |
|---|---|---|---|
| 0.417 g Melatonin | 2.500 g Poly (vinyl alcohol) 4-88 0.0667 g PEG 1000 | 0.008 g Neohesperidin dihydrochalcone 0.008 g Saccharin sodium 0.042 g Peppermint flavor 0.417 g Glycerol 85% 2.083 g Rice starch 0.058 g Titanium dioxide 0.006 g Patent blue V (Stock solution: 3.1 mg/ml) | 2.1 g Ethanol 96% (V/V) 4.2 g Purified water |

Metoclopramide

Using the following components a laminate with a nominal size of 1 000.0 cm² should be obtained. From the dried laminate films with a size of 6.7 cm² were punched.

TABLE 31

| ACTIVE INGREDIENT | POLYMERS | OTHER COMPONENTS | SOLVENTS |
|---|---|---|---|
| 1.562 g Metoclopramide hydrochloride | 2.226 g Hydroypropyl-cellulose 3.709 g Copolyvidone | 0.03 g Neohesperidin 0.059 g Menthol 5.935 g Corn starch | 20.772 g Ethanol 99% (V/V) |

Neramexane

Using the following components a laminate with a nominal size of 500.0 cm² should be obtained. From the dried laminate films with a size of 6.0 cm² were punched.

TABLE 32

| ACTIVE INGREDIENT | POLYMERS | OTHER COMPONENTS | SOLVENTS |
|---|---|---|---|
| 2.143 g Neramexane mesylat | 1.833 g Poly (vinyl alcohol) 4-88 0.500 g PEG 1000 | 0.017 g Acesulfame Potassium 0.167 g Glycerol, anhydrous 0.025 g Titanium dioxide 0.833 g Rice starch 0.012 g Masking flavor 0.045 g Orange flavor 0.083 g Polysorbate 80 | 4.2 g Ethanol 96% (V/V) 5.8 g Purified water |

Olanzapine

Using the following components a laminate with a nominal size of 628.0 cm² should be obtained. From the dried laminate films with a size of 6.0 cm² were punched.

TABLE 33

| ACTIVE INGREDIENT | POLYMERS | OTHER COMPONENTS | SOLVENTS |
|---|---|---|---|
| 1.047 g Olanzapine | 2.304 g Poly (vinyl alcohol) 4-88 0.628 g PEG 1000 | 0.021 g Acesulfame Potassium | 1.5 g Ethanol 96% (V/V) 4.5 g Purified water |

Piroxicam

Using the following components a laminate with a nominal size of 2 000.0 cm² should be obtained. From the dried laminate films with a size of 5.0 cm² were punched.

TABLE 34

| ACTIVE INGREDIENT | POLYMERS | OTHER COMPONENTS | SOLVENTS |
|---|---|---|---|
| 8.000 g Piroxicam | 11.200 g Poly (vinyl alcohol) IF 14 000 2.800 g PEG 1000 | | 16.0 g Ethanol 96% (V/V) 22.4 g Purified water |

Sildenafile

Using the following components a laminate with a nominal size of 1 800.0 cm² should be obtained. From the dried laminate films with a size of 6.0 cm² were punched.

TABLE 35

| ACTIVE INGREDIENT | POLYMERS | OTHER COMPONENTS | SOLVENTS |
|---|---|---|---|
| 10.534 g Sildenafile citrate | 8.400 g Poly (vinyl alcohol) 4-88 1.950 g PEG 1000 | 0.060 g Neohesperidin 0.030 g Saccharin sodium 0.120 g Peppermint oil 0.045 g Polysorbate 80 | 12.0 g Ethanol 96% (V/V) 16.8 g Purified water |

Sodium Picosulfate

Using the following components a laminate with a nominal size of 1 350.0 cm² should be obtained. From the dried laminate films with a size of 6.0 cm² were punched.

TABLE 36

| ACTIVE INGREDIENT | POLYMERS | OTHER COMPONENTS | SOLVENTS |
|---|---|---|---|
| 1.125 g Sodium picosulfate | 4.950 g Poly (vinyl alcohol) 4-88 1.350 g PEG 1000 | 0.068 g Neohesperidin dihydrochalcone 0.068 g Titanium dioxide 2.250 g Rice starch | 11.3 g Ethanol 96% (V/V) 15.8 g Purified water |

Zinc Histidine

Using the following components a laminate with a nominal size of 2 000.0 cm² should be obtained. From the dried laminate films with a size of 6.0 cm² were punched.

TABLE 37

| ACTIVE INGREDIENT | POLYMERS | OTHER COMPONENTS | SOLVENTS |
|---|---|---|---|
| 10.443 g Zinc histidine dihydrate | 7.333 g Poly (vinyl alcohol) 4-88 1.000 g PEG 1000 4.333 g Sodium alginate | 0.040 g Acesulfame potassium | 30.0 g Purified water |

Example 8

Methods of Characterizing Crystalline forms

Instrumentation—

X-ray diffraction patterns can be obtained on a Miniflex X-ray diffractometer (Rigayu), by laying the sample on a static sample holder. The goniometer radius is 150 mm.

The X-ray tube has a copper target, with a current intensity of 15 mA and a voltage of 30 kV: the radiation generated by the Cockcroft-Walton method, is constituted by $K_{\alpha 1}$(1.540562 Å) and $K_{\alpha 2}$(1.544398 Å); nickel filter is used for the suppression of $K_\beta$ radiation (1.392218 Å).

The detector is a NaI scintillator with a beryllium window. Continuous scanning occurred using a sampling width of 0.01 deg and a scanning rate of 2 deg/minute; 2 θ range of 2÷50 deg. The sample holder was amorphous glass, and the sample was pressed with a glass plate.

Differential Scanning Calorimetry (DSC) thermograms is carried out with a DSC 821$^e$ instrument (Mettler Toledo). Temperature is set at 10° C./minute, and the nitrogen flow at 30 ml/min.

Figure 5:
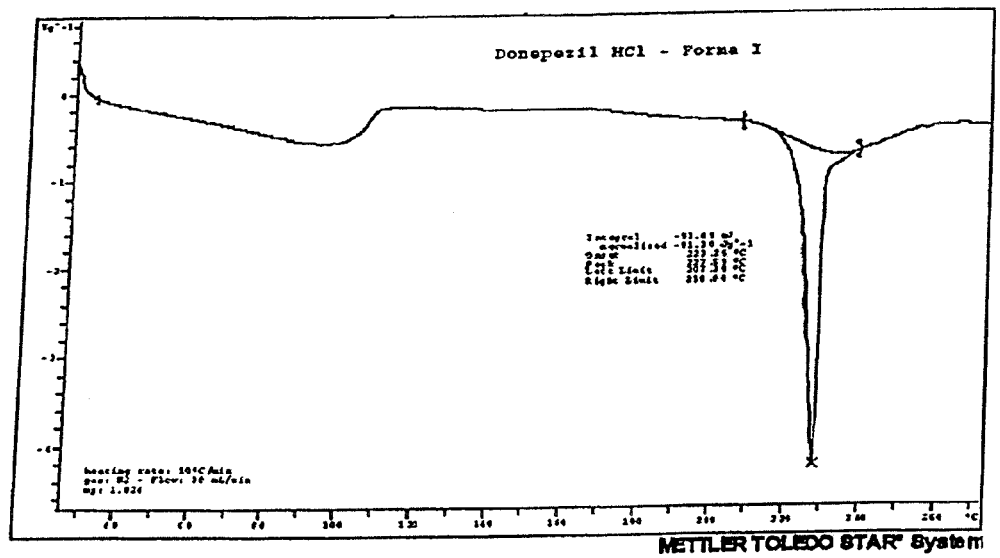
FIG. 5 is a DSC heating curve for donepezil HCl Form I.
Figure 6:
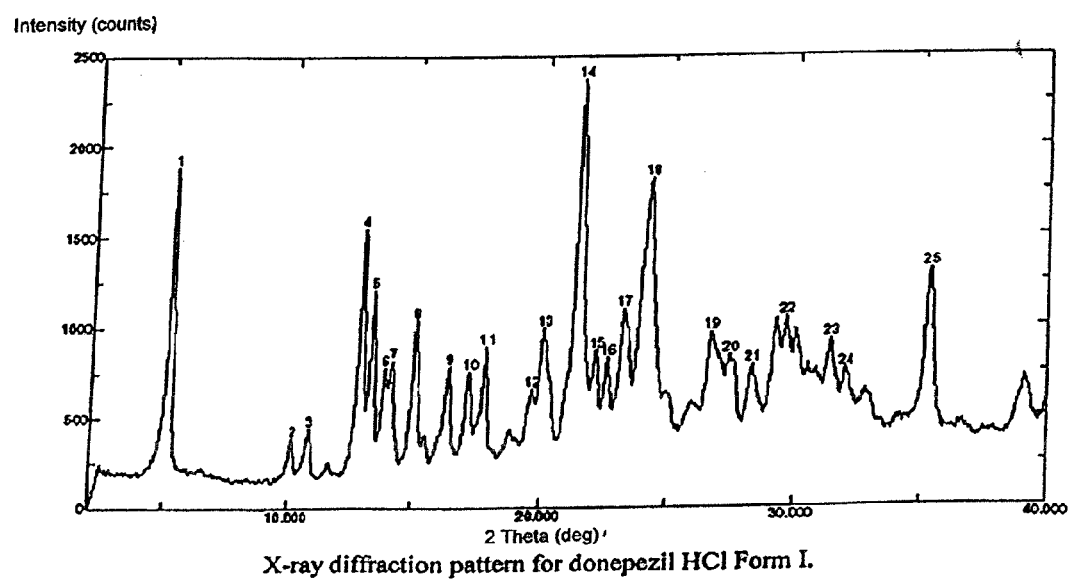
FIG. 6 is an X-ray diffraction pattern for donepezil HCl Form I.

A DSC heating curve for Donepezil HCl Form I is presented in FIG. 5; an X-ray diffraction pattern is presented in FIG. 6. X-ray diffraction peaks are given in Table 38.

TABLE 38

| Peak no. | 2theta | Flex Width | d-value | Intensity | I/Io |
|---|---|---|---|---|---|
| 1 | 5.220 | 0.188 | 16.9153 | 1890 | 80 |
| 2 | 10.140 | ***** | 8.7163 | 391 | 17 |
| 3 | 10.820 | ***** | 8.1700 | 445 | 19 |
| 4 | 12.900 | 0.235 | 6.8569 | 1548 | 66 |
| 5 | 13.340 | 0.188 | 6.6317 | 1203 | 51 |
| 6 | 13.840 | 0.165 | 6.3932 | 777 | 33 |
| 7 | 14.120 | 0.141 | 6.2671 | 814 | 35 |
| 8 | 15.060 | 0.212 | 5.8780 | 1039 | 44 |
| 9 | 16.360 | 0.188 | 5.4137 | 782 | 34 |
| 10 | 17.140 | 0.282 | 5.1691 | 756 | 32 |
| 11 | 17.760 | 0.165 | 4.9900 | 891 | 38 |
| 12 | 19.600 | 0.141 | 4.5255 | 657 | 28 |
| 13 | 20.060 | 0.141 | 4.4227 | 993 | 42 |
| 14 | 21.440 | 0.282 | 4.1411 | 2366 | 100 |
| 15 | 22.160 | 0.259 | 4.0081 | 872 | 37 |
| 16 | 22.600 | 0.141 | 3.9311 | 830 | 36 |
| 17 | 23.220 | 0.212 | 3.8275 | 1095 | 47 |
| 18 | 24.180 | 0.188 | 3.6777 | 1822 | 78 |
| 19 | 26.660 | 0.188 | 3.3409 | 966 | 41 |
| 20 | 27.420 | 0.094 | 3.2500 | 841 | 36 |
| 21 | 28.320 | 0.235 | 3.1487 | 786 | 34 |
| 22 | 29.680 | 0.094 | 3.0075 | 1047 | 45 |
| 23 | 31.440 | 0.141 | 2.8430 | 922 | 39 |
| 24 | 32.040 | 0.071 | 2.7911 | 752 | 32 |
| 25 | 35.320 | 0.353 | 2.5391 | 1305 | 56 |

Figure 7:
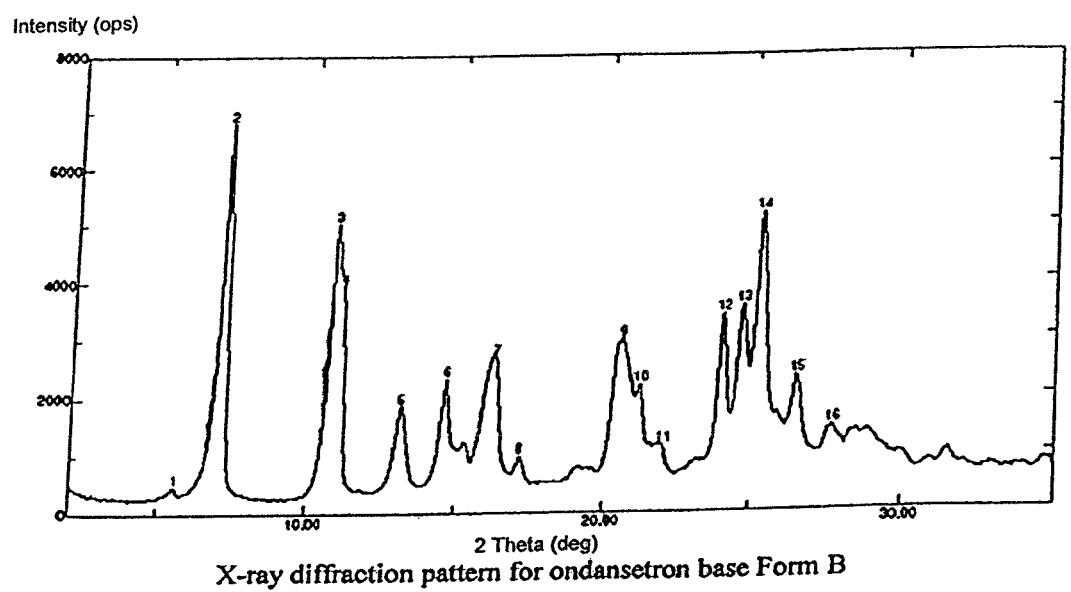
FIG. 7 is an X-ray diffraction pattern for ondansetron base Form B.

An X-ray diffraction pattern for ondansetron base Form B is depicted in FIG. 7; X-ray diffraction peaks are reported in Table 39.

TABLE 39

| Peak no. | 2theta | Flex Width | d-value | Intensity | I/Io |
|---|---|---|---|---|---|
| 1 | 5.560 | ***** | 15.8817 | 477 | 8 |
| 2 | 7.160 | 0.188 | 12.3359 | 6800 | 100 |
| 3 | 10.860 | 0.212 | 8.1400 | 5031 | 74 |
| 4 | 11.120 | 0.235 | 7.9502 | 3949 | 59 |
| 5 | 13.140 | 0.259 | 6.7322 | 1855 | 28 |
| 6 | 14.640 | 0.188 | 6.0456 | 2315 | 35 |
| 7 | 16.320 | 0.306 | 5.4269 | 2690 | 40 |
| 8 | 17.180 | 0.212 | 5.1571 | 968 | 15 |
| 9 | 20.600 | 0.188 | 4.3080 | 2995 | 45 |
| 10 | 21.220 | 0.212 | 4.1835 | 2184 | 33 |
| 11 | 22.020 | 0.141 | 4.0333 | 1150 | 17 |
| 12 | 23.980 | 0.235 | 3.7079 | 3420 | 51 |
| 13 | 24.660 | 0.259 | 3.6072 | 3563 | 53 |
| 14 | 25.260 | 0.306 | 3.5228 | 6176 | 77 |
| 15 | 26.500 | 0.282 | 3.3607 | 2324 | 35 |
| 16 | 27.700 | 0.165 | 3.2178 | 1443 | 22 |

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A non-mucoadhesive orally disintegrating film, able to disintegrate upon contact with saliva in the buccal cavity within about sixty seconds, comprising ondansetron or a pharmaceutically acceptable salt thereof in combination with a hydrophilic binder and a water-soluble diluent, wherein:
   a) said film comprises from about 4 to 24 mg ondansetron or a pharmaceutically acceptable salt thereof;
   b) said ondansetron or pharmaceutically acceptable salt thereof is present in an amount of from about 0.05% to about 50% (w/w/), based on the total weight of the film;
   c) said film has a Tmax of from about 1.0 to about 2.5 hours;
   d) said ondansetron or pharmaceutically acceptable salt thereof has an absolute bioavailability in said film of about 45-75%; and
   e) wherein the said film further comprises means for retarding absorption of active ingredient through the oral mucosa wherein the means for retarding the absorption of active ingredient through the oral mucosa are selected from the group consisting of: (1) an ion exchange resin that binds ondansetron and prevents its ionization and dissolution upon disintegration of the film, wherein said ion exchange resin is selected from the group consisting of polymers and copolymers of acrylic acid, methacrylic acid, sulfonated styrene, sulfonated divinylbenzene, dextrans, and silica gel modified by the addition of ionic groups; (2) pH adjusting agents; (3) cyclodextrin or acrylate polymers; and (4) ondansetron in base form; wherein said retarding means are able to deliver greater than 60% of said ondansetron to the gastrointestinal tract when the film is placed on the tongue, allowed to disintegrate and subsequently swallowed.

2. The non-mucoadhesive orally disintegrating film of claim 1, wherein said retarding means are able to deliver greater than 70% of said ondansetron to the gastrointestinal tract when the film is placed on the tongue, allowed to disintegrate, and subsequently swallowed.

3. The non-mucoadhesive orally disintegrating film of claim 1, wherein said retarding means are able to deliver greater than 80% of said ondansetron to the gastrointestinal tract when the film is placed on the tongue, allowed to disintegrate, and subsequently swallowed.

4. The non-mucoadhesive orally disintegrating film of claim 1, wherein said retarding means are able to deliver greater than 90% of said ondansetron to the gastrointestinal tract when the film is placed on the tongue, allowed to disintegrate, and subsequently swallowed.

5. The non-mucoadhesive orally disintegrating film of claim 1, wherein said retarding means are able to deliver greater than 95% of said ondansetron to the gastrointestinal tract when the film is placed on the tongue, allowed to disintegrate, and subsequently swallowed.

6. The non-mucoadhesive orally disintegrating film of claim 1, wherein the ondansetron comprises Form B ondansetron.

7. The non-mucoadhesive orally disintegrating film of claim 1, comprising either 4 mg or 8 mg of ondansetron.

8. The non-mucoadhesive orally disintegrating film of claim 1, wherein the film is a single layer homogenous film, having a weight from about 40 to about 120 milligrams, a thickness of from 10 to 200 microns, and a surface area of less than 7 $cm^2$.

9. The non-mucoadhesive orally disintegrating film of claim 1, wherein the film comprises ondansetron, polyvinylalcohol, polyethylene glycol, glycerol anhydrous, rice starch, acesulfam K, titanium dioxide, menthol and polysorbate.

10. The non-mucoadhesive orally disintegrating film of claim 1, wherein the film comprises 8.0 mg ondansetron, 22.0 mg polyvinylalcohol, 6.0 mg polyethylene glycol, 2.0 mg glycerol anhydrous, 10.0 mg rice starch, 0.2 mg acesulfam K, 0.3 tug titanium dioxide, 1.0 mg menthol, and 1.0 mg polysorbate.

11. The non-mucoadhesive orally disintegrating film of claim 1 for use in the treatment or prevention of emesis.

12. A non-mucoadhesive orally disintegrating film, able to disintegrate upon contact with saliva in the buccal cavity within about 60 seconds, comprising ondansetron in combination with a hydrophilic binder and a water soluble diluent, wherein:
   a) said film comprises about 4 or about 8 mg ondansetron in the form of a free base;
   b) said ondansetron is present in an amount of from about 0.05% to about 50% (w/w), based on the total weight of the film; and
   c) said film has a Tmax of from about 1.0 to about 2.5 hours;
   d) said ondansetron has an absolute bioavailability in said film of about 45-75%; and
   e) wherein said film comprises means for retarding absorption of active ingredient through the oral mucosa wherein the means for retarding the absorption of active ingredient through the oral mucosa are selected from the group consisting of: (1) an ion exchange resin that binds ondansetron and prevents its ionization and dissolution upon disintegration of the film, wherein said ion exchange resin is selected from the group consisting of polymers and copolymers of acrylic acid, methacrylic acid, sulfonated styrene, sulfonated divinylbenzene, dextrans, and silica gel modified by the addition of ionic groups; (2) pH adjusting agents; (3) cyclodextrin or acrylate polymers; and (4) ondansetron in base form; wherein said retarding means are able to deliver greater than 60% of said ondansetron to the gastrointestinal tract when the film is placed on the tongue, allowed to disintegrate, and subsequently swallowed.

* * * * *